United States Patent
Dixit et al.

(10) Patent No.: US 12,396,954 B2
(45) Date of Patent: Aug. 26, 2025

(54) SOFT-CHEW TABLET PHARMACEUTICAL FORMULATIONS

(71) Applicant: First Time US Generics LLC, Broomall, PA (US)

(72) Inventors: Manesh A Dixit, Miami Lakes, FL (US); Partha S Sen, Valsad (IN); Rahul G Raut, Pune (IN)

(73) Assignee: USPHARMA LTD, Miami Lakes, FL (US)

( * ) Notice: Subject to any disclaimer, the term of this patent is extended or adjusted under 35 U.S.C. 154(b) by 304 days.

(21) Appl. No.: 17/893,265

(22) Filed: Aug. 23, 2022

(65) Prior Publication Data

US 2022/0409547 A1    Dec. 29, 2022

Related U.S. Application Data

(63) Continuation-in-part of application No. 16/894,514, filed on Jun. 5, 2020, now Pat. No. 11,633,361, which is a continuation of application No. 16/140,477, filed on Sep. 24, 2018, now abandoned, which is a continuation-in-part of application No. 15/629,354, filed on Jun. 21, 2017, now Pat. No. 10,117,831, which is a continuation-in-part of application No. PCT/US2016/067443, filed on Dec. 19, 2016.

(60) Provisional application No. 62/269,951, filed on Dec. 19, 2015.

(51) Int. Cl.
| | |
|---|---|
| *A61K 9/20* | (2006.01) |
| *A61K 9/00* | (2006.01) |
| *A61K 31/167* | (2006.01) |
| *A61K 31/192* | (2006.01) |
| *A61K 31/403* | (2006.01) |
| *A61K 31/415* | (2006.01) |
| *A61K 31/496* | (2006.01) |
| *A61K 31/501* | (2006.01) |
| *A61K 31/5395* | (2006.01) |
| *A61K 31/546* | (2006.01) |

(52) U.S. Cl.
CPC .......... *A61K 9/2095* (2013.01); *A61K 9/0056* (2013.01); *A61K 9/2009* (2013.01); *A61K 9/2018* (2013.01); *A61K 9/2054* (2013.01); *A61K 9/2059* (2013.01); *A61K 9/2068* (2013.01); *A61K 9/2081* (2013.01); *A61K 31/167* (2013.01); *A61K 31/192* (2013.01); *A61K 31/403* (2013.01); *A61K 31/415* (2013.01); *A61K 31/496* (2013.01); *A61K 31/501* (2013.01); *A61K 31/5395* (2013.01); *A61K 31/546* (2013.01)

(58) Field of Classification Search
CPC .. A61K 9/2095; A61K 9/0056; A61K 9/2009; A61K 9/2018; A61K 9/2054; A61K 9/2059; A61K 9/2068; A61K 9/2081; A61K 31/167; A61K 31/192; A61K 31/403; A61K 31/415; A61K 31/496; A61K 31/501; A61K 31/5395; A61K 31/546; A61K 47/10; A61K 47/12; A61K 47/26; A61K 47/32; A61K 47/34; A61K 47/36; A61K 47/44
See application file for complete search history.

(56) References Cited

U.S. PATENT DOCUMENTS

2019/0022013 A1*    1/2019    Dixit .................... A61K 31/415

FOREIGN PATENT DOCUMENTS

| CN | 110200931 A | * | 9/2019 | ........... A61K 31/592 |
| WO | wo2017106812 | * | 6/2017 | ............... A61K 9/00 |

* cited by examiner

*Primary Examiner* — Robert A Wax
*Assistant Examiner* — Kimberly Barber
(74) *Attorney, Agent, or Firm* — West Law Office LLC

(57) ABSTRACT

A product and process of manufacturing an edible soft-chewable dosage form for the delivery of pharmaceutically active ingredients or nutritional agents orally to an animal or human subject, by forming a granulated soft-chew mass by appropriate mixing and sifting steps, and forming tablets with a compression press. Such soft-chew dosage forms have hardness of less than about two kilopond (2 kp) and friability of less than about one percent (1%) at three-hundred (300) rotations when measured according to the United States Pharmacopeia (USP) test. The process for manufacturing such compressed soft-chew tablets employs compression (tablet) pressing equipment to produce soft-chew tablets of consistent weight and texture.

3 Claims, 1 Drawing Sheet

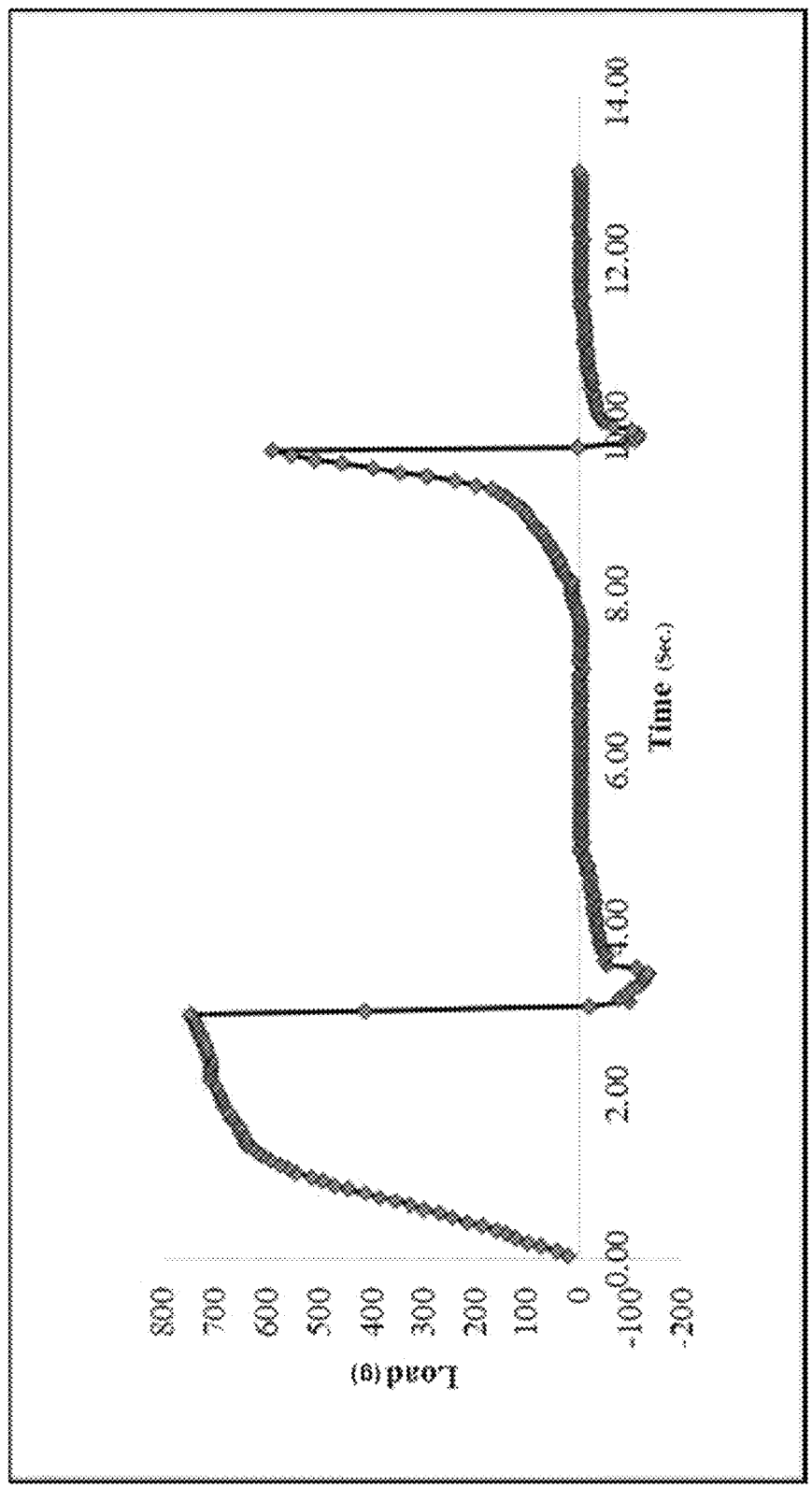

SOFT-CHEW TABLET PHARMACEUTICAL FORMULATIONS

RELATED APPLICATIONS

The present application is a continuation-in-part of U.S. patent application Ser. No. 16/894,514 filed Jun. 5, 2020, entitled Soft Chew Pharmaceutical Formulations, which is a continuation of U.S. patent application Ser. No. 16/140,477 filed Sep. 24, 2018, entitled Soft Chew Pharmaceutical Formulations, which is a continuation-in-part of U.S. patent application Ser. No. 15/629,354 filed Jun. 21, 2017, entitled Soft Chew Pharmaceutical Formulations, which is a continuation-in-part of International Patent Application No. PCT/US2016/067443 filed Dec. 19, 2016, entitled Soft Chew Pharmaceutical Formulations, which claims the benefit of U.S. Provisional Patent Application Ser. No. 62/269,951, filed Dec. 19, 2015, entitled Soft Chew Tablets; and claims the benefit of U.S. Provisional Patent Application Ser. No. 63/333,159, filed Apr. 21, 2022, entitled Tablet Press Compression Tooling Assembly, each of which is hereby incorporated in its entirety by reference herein.

BACKGROUND

1. Field

The present invention relates to products and processes for the manufacture of soft-chewable tablet pharmaceutical or nutritional dosage forms, for the oral administration of active pharmaceutical ingredients or nutritional agents.

2. Discussion of Prior Art

Chewable pharmaceutical dosage units, such as chewable tablets and soft-chewable tablets, are known and have been commercialized for use with pediatric, geriatric, and involuntary patient populations. Such dosage forms have also been used for subjects that, by instinct, will not accept medication meant to be swallowed. Chewable tablets are also useful with competent patients as an alternative to tablets or capsules that must be swallowed whole. The formulation of a drug into a chewable dosage form can increase patient acceptance of a medication in patients that resist or are unable to swallow conventional tablets or capsules.

Oral dosage forms, such as chewable compressed tablets, formulated using conventional ingredients tend to be gritty or otherwise unappealing to many patients. Traditionally, tablets compressed on a compression machine are formulated to produce tablets having a hardness of more than ten kiloponds (10 kp). Tablets having lower hardness levels (i.e., less than 10 kp) are often discouraged by the prior art to enable formation of tablets having friability values within acceptable ranges.

A process for manufacturing soft-chewable dosage form for drug delivery is described in U.S. Pat. No. 6,387,381. It discloses a soft-chewable medication vehicle for drug delivery of an active ingredient to animal or human subjects, not containing ingredients of animal origin, without the use of heat and without the addition of water. The formed mixture was formed into individual chunks using a Formax F6™ molding machine with dies for production of chunk-like shapes, and packaged for storage. Machines for the production of molded food patties have been described as being useful for the manufacturing of soft-chews for administration to non-human animals. Such machines are molding machines that have been originally developed for use in producing molded food products, for example the Formax F6™ molding machine made by the Formax Corporation.

The use of extruders, forming machines, and rotary molding machines to manufacture pharmaceutical tablets can be problematic. For instance, it is difficult to control the weight and physical form of tablets formed by such devices. Typically, excessive conditioning of the initial tablet structure (e.g., drying or curing) after formation using such devices is required to achieve the desired shape and structure of the finished tablet. Moreover, the use of such technologies, equipment, and processes is complex, cumbersome, and not traditionally employed by typical pharmaceutical manufacturing facilities producing solid oral dosage forms.

Thus, there is a need for soft-chew tablet formulations, and processes of making the same, that enable large scale manufacture using equipment traditionally employed in the pharmaceutical manufacturing industry; including, but not limited to, rotary (tablet) compression presses.

This background discussion is intended to provide information related to the present invention which is not necessarily prior art.

SUMMARY OF THE INVENTION

The present invention overcomes the disadvantages and shortcomings of known chewable dosage forms, and known processes for making the same, by providing a simplified process for manufacturing soft-chewable dosage units using conventional pharmaceutical equipment and compression techniques (e.g., a rotary tablet press).

Dosage forms of the present invention include palatable, soft-chewable pharmaceutical compositions for oral administration to an involuntary subject population (e.g., very young children, senile patients, animals, etc.) that includes a therapeutically effective amount of a pharmaceutically active ingredient, in an immediate or controlled release form, and a palatability improving agent in an amount sufficient to make the pharmaceutical composition palatable to the subject population. As used herein, the phrase "involuntary subject population" is defined as patients who cannot be conventionally instructed to chew and/or swallow conventional hard chew tablets or capsules.

The texture of a chewable dosage form is an important factor in the acceptance of oral dosage forms by patients in need of medication. Soft-chewable tablets, having a soft texture, pleasant mouthfeel, and palatable taste with adequate flavoring agents, provide a solution to such problems. In addition, these features can address the problem of the disagreeable taste of many active pharmaceutical ingredients. The soft-chew dosage forms of the present invention are formulated to address texture problems attributed to the dry, dusty, granular, and pulverant nature of many pharmaceutical ingredients.

The soft-chewable pharmaceutical dosage units (soft-chew tablets) of the present invention are solid at room temperature and have lower hardness and higher moisture content relative to conventional tablets or hard-chew tablets. The soft-chew tablets of the present invention have a soft texture, low hardness, are designed to be chewed and swallowed, and will not appreciably dissolve in the mouth of the patient. The soft-chew tablets of the present invention exhibit a plastic rheological behavior and can be formed into many different shapes using a wide range of manufacturing processes. After formation, the soft-chew tablets of the present invention are dimensionally stable.

In certain embodiments, the soft-chew tablets of the present invention are prepared using conventional methods, such as wet or dry granulation processes. Preferably, the soft-chew tablets of the present invention are formulated using pharmaceutical grade ingredients.

It has been found that soft-chew tablets of the prior art can be manufactured more efficiently, reliably, and consistently, using a tablet press. The compressed soft-chew dosage forms of the present invention have hardness values of less than 2 kp, or may have hardness values of less than 1 kp, or may have no measurable hardness when measured with a tablet hardness tester. Despite their low hardness, the soft-chew tablets of the present invention exhibit friability values of less than 1.0%, or less than 0.5%, or less than 0.1% when determined in accordance with the USP friability test at 100-rotations, 200-rotations, or 300-rotations.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing FIGURES.

BRIEF DESCRIPTION OF THE DRAWING FIGURES

FIG. 1. is a plot of the texture profile analysis of the soft-chew tablet made in accordance with Example 9.

DETAILED DESCRIPTION OF THE PREFERRED EMBODIMENTS

In addition to the other terms expressly defined herein, for the purposes of this disclosure and claims, the following terms, units, words, and phrases shall have the respective meanings assigned to them as follows (and cognate expressions shall bear corresponding meanings): the unit symbol "N" means Newton, the International System of Units (SI) unit of measurement for force; the unit symbol "kp" means kilopond(s), a unit of measurement for tablet hardness, which is sometimes referred to as a kilogram-force (kfg) and is equal to 9.80665 N; the unit symbol "kfg" means kilogram-force, a gravitational metric unit of force equal to 9.80665 N; the unit symbol "SC" means Strong-Cobb, a unit of measurement for tablet hardness, which is equal to approximately 0.7 kilogram of force or about 7 N; the unit symbol "lb" means pound, a unit of measurement for tablet hardness; the unit symbol "kg" means kilogram(s), the SI unit of mass; the unit symbol "g" means gram(s), a unit of mass equal to 0.001 kg; the unit symbol "mg" means milligram(s), a unit of mass equal to 0.000001 kg; the unit symbol "mL" means milliliter, a unit of volume equal to 0.000001 cubic meters; the unit symbol "mm" means millimeter; the unit symbol "µ" means micron, which is equal to 0.001 mm; the unit symbol "° C." means degree(s) in Celsius, a unit of temperature on the Celsius scale; the unit symbol "% w/w" means percent-by-weight, the amount/concentration of one or more components in a group of components, which can be calculated by dividing the numerical value for the mass of one or more components in a group of components by the numerical value for the mass of all of the components in the group and multiplying the quotient by 100; the phrase "USP friability test" means the harmonized standard for determination of compressed tablet friability provided in general chapter <1216> of the United States Pharmacopeia, which is hereby incorporated in its entirety by reference herein (it is particularly noted that the USP friability test calls for 100-drum-rotations; however, if a friability value is provided herein for a greater number of drum rotations, it should be understood that all other guidelines for determining friability under general chapter <1216> were followed to obtain such friability value); the phrase "USP disintegration test" means the harmonized standard for determination of whether a tablet will disintegrate within the prescribed time when placed in a liquid medium as provided in general chapter <701> of the United States Pharmacopeia, which is hereby incorporated in its entirety by reference herein; the term "PTFE" means the compound polytetrafluoroethylene; the term "POM" means the compound polyoxymethylene; the term "EDTA" means the compound sodium ethylenediaminetetraacetic acid; the term "NSAID" means a non-steroidal anti-inflammatory drug; the term "FDA" means the U.S. Food and Drug Administration; the phrase "active ingredient" means an active pharmaceutical ingredient or a nutritional agent (an active ingredient may be in granular form and coated, or further coated, with a suitable coating. For example, the coating could be a coating polymer that coats and protects the active ingredient, or masks an offensive taste and/or offensive odor. In certain embodiments, the coating could be a functional coating (e.g., an extended-release coating, delayed-release coating, controlled-release coating, barrier coating, or a combination thereof)); the phrase "active agent" means an active ingredient; the phrase "active pharmaceutical ingredient" means a substance used in a pharmaceutical dosage form, intended to furnish pharmacological activity or to otherwise have direct effect in the diagnosis, cure, mitigation, treatment or prevention of disease, and substances that have, or are thought to have, a direct effect in restoring, correcting, or modifying physiological functions in a patient population (an active pharmaceutical ingredient may include any approved or experimental drug. By "approved," it is meant that the drug is approved for human or veterinary use by a regulatory agency in any country that makes such drug approvals. For example, the pharmaceutically active ingredient may be selected from an anesthetic agent, anthelmintic agent, analgesic agent, steroid, corticosteroid agent, non-steroidal anti-inflammatory drug (NSAID) agent, antiemetic agent, antithyroidal agent, parasiticidal agent, appetite stimulant, antihistamine agent, antifungal agent, antiprotozoal agent, or anti-depressant); the term "API" means active pharmaceutical ingredient; the phrase "nutritional agent" means minerals, vitamins, nutraceutical agents, and other supplements, including derivatives, salts (and the like), and/or mixtures of the foregoing; the phrase "soft-chew tablet" means a solid, soft chewable, semi-plastic oral dosage form for the delivery of an active ingredient; and the term "fluid" means a material that is flowable or malleable fluid material may be a viscous liquid, with a viscosity comparable, for example, to water, vegetable oil, honey, or peanut butter.

The inventors have discovered that by stepwise formulation according to the present invention, conventional tablet compression techniques (such as a tablet press) can be used to form very soft tablets with a uniform composition.

In certain embodiments of the present invention, dosage forms are formed by making a soft chew mass. The soft chew mass includes various excipients including softening agent(s), humectant(s), dry ingredients, granulation ingredients (granulation aid ingredients and intra-granulation ingredients), extra-granulation ingredients, and active ingredients. During the granulation process, granules of the soft chew mass are formed, passed through appropriate screens for sizing, and lubricated with extra granular excipients then compressed using a tablet press.

Soft-chew tablets of the present invention have a soft texture, low hardness, and may be chewed and swallowed. The texture of the soft-chew tablet is such that it does not appreciably dissolve in the mouth. Soft-chew tablets of the present invention may be designed to be chewed and swallowed by a human or an animal.

In certain embodiments of the present invention, soft-chew tablets are manufactured by a process of: (a) mixing at least one active ingredient with at least one dry or liquid component to form a liquid; (b) blending dry ingredients having at least one of each of a bulking agent, a lipid, a flavoring agent, a disintegrating agent, a texturing agent, a binding agent, a preservative, a lubricating agent, an anti-sticking agent, and, optionally, a surfactant to form a uniform dry ingredient mixture; (c) blending the premix and the uniform dry ingredient mixture to form a granulated compacted soft-chew mass; (d) sifting the granulated compacted soft-chew mass through at least one sifting screen to form uniform granules of the soft-chew mass; and (e) adding a lubricant or anti sticking agent to the uniform granules of the soft-chew mass and compressing the resulting mixture in a tablet press to form soft-chew tablets.

In certain embodiments of the present invention, two or more mixtures are prepared in the inventive process. One mixture is a fluid premix containing the active ingredient, and the other mixture is a blend of dry ingredients. The fluid premix and dry ingredient blend are mixed together to form a soft-chew mass.

Texturing agents are additives present in formulations in order to primarily enhance the consistency and the soft feel of the finished product. In certain embodiments of the present invention, texturing agents are used to improve the overall texture or mouthfeel of the soft-chew tablets. In certain embodiments, texturing agents are present in the formulation in concentrations ranging from about 5% w/w to about 50% w/w. In certain embodiments, the composition of the soft-chew tablets of the present invention include a texturing agent, selected from the group including, comprising modified corn starches, poly(ethylene) oxide, microcrystalline cellulose, modified microcrystalline cellulose, corn syrup solids, dried glucose syrup, maltodextrin, partially hydrogenated guar gum (PHGG), milk powder, *solanum* starch, and the like.

In certain embodiments, the composition of the soft-chew tablets of the present invention include one or more fillers. A filler may be used to increase the total mass of the chewable formulation to a manageable size or to enhance the flow properties of the final powder or granules to be compressed.

In certain embodiments, the composition of the soft-chew tablets of the present invention include a binding agent. The binding agent may be polyethylene glycol. The polyethylene glycol may be admixed to dry ingredients for mixing. The polyethylene glycol may be melted and added to at least one other dry ingredient and mixed to form the uniform dry ingredient mixture.

In certain embodiments, the composition of the soft-chew tablets of the present invention include microcrystalline cellulose as a bulking agent.

In certain embodiments, the composition of the soft-chew tablets of the present invention include a lipid and microcrystalline cellulose in a ratio of about 2:1 to about 1:2.5, weight-by-weight, and wherein the tablet is manufactured by compression on a tablet press.

In certain embodiments of the present invention, one or more diluents may be used in combination with silicified microcrystalline cellulose. Examples of diluents include starches and their derivatives (e.g., hydrogenated starch hydrolysate), celluloses and their derivatives (e.g., cellulose acetate), protein matrices (e.g., soy protein, dextrates, wheat gluten, whey, corn cob, corn gluten), carbohydrates (e.g., maltodextrin, polydextrose), sugars and sugar alcohols (e.g., glucose, lactose, fructose, maltose, dextrose, sucrose, maltitol, xylitol, isomalt, mannitol), silicates, dextrates, kaolin, polymethacrylates, talc, salts (e.g., calcium phosphates, calcium sulfate, magnesium carbonate) or any combination of any two or more thereof.

In certain embodiments, the composition of the soft-chew tablets of the present invention includes a starch, or a modified starch, or a mixture of starch and modified starch.

In certain embodiments, the composition of the soft-chew tablets of the present invention includes one or more binders. Binders improve the binding properties of the compacted mass, to assist the formation of compact dosage units. Any suitable binder known in the art may be used. For example, binders that may be used according to the present invention may include, but are not limited to, gums (e.g., xanthan gum and guar gum), alginates, celluloses and their derivatives (e.g., methylcellulose and microcrystalline cellulose), lipids (e.g., fats and oils), starches and their derivatives, dextrins, povidones, silicates, polymethacrylates, polyethylene oxides, waxes, chitosan, polycarbophil, agar, carbomers, and combinations of the foregoing.

In certain embodiments, the composition of the soft-chew tablets of the present invention includes one or more palatability enhancers. Palatability enhancers improve the taste of a material. Advantageously, palatability enhancers may improve the palatability of soft-chew tablet formulations comprising bitter, acrid, obnoxious, unpleasant, or otherwise unpalatable active agents.

In certain embodiments of the present invention, the palatability enhancer is a taste masking agent, a flavoring agent, an aroma modifier, or a taste modifier, or any combination of any two or more thereof.

Flavoring agents may be used to improve the palatability of the soft-chew tablets of the present invention. Any type of flavoring agent can be used provided it improves the palatability of the product, typically by improving its taste and/or smell. The use of a flavoring agent may also assist with dose compliance. Flavors can be natural (derived from animal or plant sources), semisynthetic, or artificial. In one embodiment, the flavoring agent is an artificial flavoring agent, semi-synthetic flavoring agent, a natural flavoring agent, or nature identical flavoring agent. In certain preferred embodiments of the present invention, flavoring agents are present in a concentration ranging from about two 2% w/w to about 30% w/w. Suitable flavoring agents include, but are not limited to, spray dried banana powder, mixed fruit powder, pineapple powder, strawberry powder, watermelon powder, honey powder, cocoa powder, grape powder, raspberry powder, mixed berry powder, orange powder, mango powder, mushroom powder, etc. In certain embodiments of the present invention, a taste modifier is used to improve the taste of the soft-chew tablets. In certain embodiments, the composition of the soft-chew tablets of the present invention includes a taste modifier selected from the group comprising citric acid, malic acid, lactic acid, hydroxypropyl-β-cyclodextrin, bitter masker, bitter blocker, calcium carboxy methyl cellulose, etc.

In certain embodiments, the composition of the soft-chew tablets of the present invention includes liquid components that are absorbed on the surface of a lipid absorbing pharmaceutical ingredient selected from one or more of microcrystalline cellulose, silicified microcrystalline cellulose, and a combination of microcrystalline cellulose and guar gum. The liquid components absorbed on the surface of the lipid absorbing pharmaceutical ingredient may be mixed with the dry ingredient mixture and then sifted again through at least one sifting screen to form further granules of the soft-chew composition mixture. In an embodiment, a nutritional agent or a pharmaceutically active ingredient is admixed with the liquid components prior to mixing with the lipid absorbing pharmaceutical ingredient.

In certain embodiments of the present invention, plasticizers may be added to the formulation to improve plasticity and malleability of the soft-chew tablets of the present invention. In certain embodiments, a plasticizer may be selected from alcohols, glycols (such as propylene glycol), lanolin, wool fat, liquid paraffin, mineral oil, petrolatum, benzyl phenylformate, chlorobutanol, diethyl phthalate, glycerol, polyethylene glycol, sorbitol, triacetin, benzyl phenyl formate, dibutyl sebacate, tributyl citrate, triethyl citrate, or any combination of any two or more thereof. Other plasticizers known in the art may also be used.

In certain embodiments, the composition of the soft-chew tablets of the present invention includes a non-active ingredient including one or more of a starch, a polysaccharide, a humectant, a polyol, water-soluble poly(ethylene oxide) resin.

In certain embodiments, the composition of the soft-chew tablets of the present invention includes a humectant. A humectant is used to retain moisture in the dosage unit. Humectants may be selected from sugars, hydrogenated starch hydrolysate, etc. Suitable liquid humectants include, but are not limited to, glycols, polyols, sugar alcohols, corn syrup or any combination of any two or more thereof. Other humectants known in the art may also be used.

In certain embodiments, the composition of the soft-chew tablets of the present invention includes an antioxidant. An antioxidant inhibits oxidation and may be of benefit as a preservative, or to maintain the chemical stability of an active or inactive ingredient. An antioxidant may be selected from propyl gallate, ascorbic acid and its derivatives, sodium formaldehyde sulfoxylate, malic acid, fumaric acid, editic acid, thiols, polyphenols, EDTA, sodium ascorbate, sodium metabisulfite, butylated hydroxytoluene, butylated hydroxyanisole, butylated hydroxyanisole and butylated hydroxytoluene co-processed with *Zea mays* oil or natural substances such as flavonoids, tocopherols, carotenes, cysteine, or any combination of any two or more thereof. Other antioxidants known in the art may also be used. The antioxidants are generally added to the formulation in amounts ranging from about 0.01% w/w to about 2% w/w, with amounts ranging from about 0.01% w/w to about 1.0% w/w being especially preferred.

In certain embodiments, the composition of the soft-chew tablets of the present invention includes a preservative selected from the group including parabens (e.g., methylparaben and/or propylparaben), benzalkonium chloride, benzethonium chloride, benzoic acid, citric acid, fumaric acid, bronopol, butylparaben, cetrimide, chlorobutanol, chlorocresol, cresol, ethylparaben, imidurea, phenol, phenoxyethanol, phenylethyl alcohol, potassium sorbate, sodium benzoate, sodium propionate, and sorbic acid. Other preservatives known in the art may also be used.

In certain embodiments, the composition of the soft-chew tablets of the present invention includes a nonaqueous solvent, for example glycerin or propylene glycol. A non-aqueous solvent may disperse, solubilize, or enhance solubilization of an active ingredient. The non-aqueous solvent may also enhance the binding of the formulation and/or the consistency and texture of the soft-chewable dosage form.

In certain embodiments, the composition of the soft-chew tablets of the present invention includes a disintegrating agent. A disintegrating agent may be used to enable the inventive chewable tablets to break down on contact with water, saliva, or gastric fluid in the stomach to quickly release the active ingredient. A disintegrating agent may be selected from cross-linked povidones, croscarmellose sodium, sodium starch glycollate, celluloses and their derivatives, starches and their derivatives, gelatin, silicon dioxide, or any combination of any two or more thereof. Other disintegrating agents known in the art may also be used. Disintegration may be tested and measured in accordance with the USP disintegration test, using water as the medium.

In certain embodiments of the present invention, a granulated compacted soft-chew mass is formed, and the mass is dried by equipment using direct or indirect conduction heat applied to a static solid bed, a moving solid bed, or a fluidized solid bed. The granulated mass may be dried at room temperature, for example about 25° C. plus-or-minus 10° C. or may be dried at a controlled temperature of about 50° C. or less. In certain embodiments, no heating for drying is employed to form the soft-chew tablets.

In certain embodiments of the present invention, the process of manufacturing soft-chew tablets may include sifting, or milling, of dry components or a granulated mass, or a mixture of both through sifting screens with mesh sizes commonly known in the art. Mesh sizes for sifting screens may include Mesh #4 or 5 or 6 or 7 or 8 or 10 or 12 or 14 or 16 or 18 or 20 or 25 or 30 or 35 or 40 or 45 or 50 or 60 or other mesh sizes commonly known in the art. Components may be sifted through at two or more screens with different mesh sizes one after other in gradual or random order of mesh sizes.

In certain embodiments of the present invention, the dry ingredient mixture or the granulated compacted soft-chew mass is sifted through sifting equipment using impaction, attrition, compression, or cutting.

In certain embodiments of the present invention, the dry ingredient mixture or the granulated compacted soft-chew mass is uniformly mixed using equipment providing diffusion mixing, convection mixing, or pneumatic mixing.

In certain embodiments of the present invention, a pre-compression force may be applied to the granulated compacted soft-chew mass before application of the primary compression force that forms the soft-chew tablet.

In certain embodiments of the present invention, the granulated compacted soft-chew mass may be fed into a compression die by gravity feed, power assisted feed, by centrifugal force, or by compression coating.

In certain embodiments of the present invention, the soft-chew tablets may incorporate an abuse-deterrent technology, which can include one or more high-melting-point excipients that resist heating and injecting; taste modifiers that resist covert administration, snorting (i.e., ingestion of a powdered material through the nose) and dose dumping (i.e., extraction of active pharmaceutical ingredients (API) from tablets); water insoluble excipients that resist extraction and drink adulteration; waxy excipients that resist snorting; viscosity modifiers that resist dissolution, injection and dose dumping; low-density excipients that resist drink adulteration; and dyes, that resist adulteration.

In certain embodiments of the present invention, a soft-chew tablet is manufactured by a process of: (a) mixing an intragranular mixture with a softening agent and a granulation dispersion to form a wet mass; (b) mixing and sifting the wet mass with an extragranular mixture to form granules; (c) lubricating the first granules to form lubricated granules; and (d) compressing the lubricated granules in a tablet press to from soft-chew tablets.

In certain embodiments of the present invention, the intragranular mixture is a mixture of two or more intragranular ingredients including dried glucose syrup, mannitol, sorbitol powder, partially pregelatinized starch, partially hydrogenated guar gum (PHGG), carboxymethylcellulose calcium, *solanum* starch, monoammonium glycyrrhizinate, milk powder, croscarmellose sodium, calcium gluconate monohydrate, carnauba wax, flavor agent, maltodextrin, sodium starch glycolate, citric acid anhydrous, magnesium stearate, sodium bicarbonate, sucralose, xylitol, crospovidone, hydroxypropyl beta-cyclodextrin, potassium sorbate, sodium benzoate, sodium caseinate, Advantol 300 (co-processed excipients), albumin, granulated corn starch, dextrose anhydrous, magnesium hydroxide, silicified microcrystalline cellulose, soy protein, whey protein, and xanthan gum. In certain preferred embodiments, the intragranular mixture is formed by co-sifting the intragranular ingredients at least two times using a sieve as described in greater detail in the Examples hereinbelow.

In certain embodiments of the present invention, softening agents are used in combination with one or more humectants to enhance the softness of the soft-chew tablet. In certain embodiments of the present invention, at least one softening agent is selected from the group comprising canola oil, cocoa butter, coconut oil, corn oil, flaxseed oil, glycols (such as propylene glycol), hydrogenated vegetable oils, lanolin, lecithin, lipids, liquid paraffin, MCT oil, mineral oil, natural substances such as flavonoids, olive oil, palm oil, polyethylene glycol, rosemary oil, seed oil, simethicone, soybean oil, thyme oil, triglycerides or medium chain triglycerides (MCT), vegetable oils, wool fat, *Zea mays* oil, and other suitable lipids.

In certain embodiments of the present invention, the granulation dispersion is a combination of two or more ingredients including glycerin, maltitol solution, sucralose, *stevia* (natural sweetener), citric acid anhydrous, bitter masker, polyvinylpyrrolidone, polyethylene glycol, hydroxypropyl beta-cyclodextrin, non crystallizing sorbitol solution, soya lecithin, flavor agents, and color agents. In certain preferred embodiments, the granulation dispersion is formed by mixing two or more ingredients until a uniform granulation dispersion is formed as described in greater detail in the Examples hereinbelow.

In certain embodiments of the present invention, the wet mass is a mixture of the intragranular mixture, the lipid, and the granulation dispersion. In certain preferred embodiments, the intragranular mixture, the lipid, and the granulation dispersion are mixed using a rapid mixer granulator to form a wet mass as described in greater detail in the Examples hereinbelow.

In certain embodiments of the present invention, the extragranular mixture is a mixture of two or more extragranular ingredients including mannitol, partially pregelatinized starch, partially hydrogenated guar gum (PHGG), carboxymethylcellulose calcium, *solanum* starch, flavor agent, crospovidone, milk powder, citric acid anhydrous, xylitol, croscarmellose sodium, silicified microcrystalline cellulose, sorbitol (powder), Advantol 300 (co-processed ingredients), and granulated corn starch. In certain preferred embodiments, the extragranular mixture is formed by co-sifting the extragranular ingredients at least two times using a sieve as described in greater detail in the Examples hereinbelow.

In certain embodiments of the present invention, the wet mass is mixed with the extragranular mixture to form granules. In certain preferred embodiments, the wet mass and the extragranular mixture are mixed using a cone mill to form milled granules, as described in greater detail in the Examples hereinbelow.

In certain embodiments of the present invention, the milled granules are lubricated with a lubricating agent to form lubricated granules. In certain embodiments of the present invention, a lubricating agent is selected from at least one of carnauba wax and/or magnesium stearate. In certain preferred embodiments, the lubricated granules are formed by lubricating the milled granules as described in greater detail in the Examples hereinbelow.

In certain embodiments of the present invention, the lubricated granules are compressed to form one or more soft-chew tablets. In certain preferred embodiments of the present invention, the lubricated granules are compressed using a tablet press to form one or more soft-chew tablets. A tablet press is a mechanical device that compresses powder into tablets of uniform size and weight. A press can be used to manufacture tablets/pellets of a wide variety of materials, including pharmaceuticals, cleaning products, and cosmetics. There are two types of press machines, eccentric-type and rotary-type. The rotary-type is generally more widely used, because it facilitates high production performance with narrow weight variation along with ease of use.

In certain preferred embodiments, as provided in the Examples included hereinbelow, one or more active ingredients are included in the intragranular mixture. In certain preferred embodiments, as provided in the Examples included hereinbelow, the softening agent includes an active ingredient, such as simethicone. In certain preferred embodiments, as provided in the Examples included hereinbelow, an active ingredient is included in the granulation dispersion. In certain preferred embodiments, as provided in the Examples included hereinbelow, an active ingredient is included in the extragranular mixture.

In certain embodiments of the present invention, the active ingredient may be dissolved, emulsified, or suspended in a non-aqueous solvent before addition. The active ingredient may be soluble, partially soluble, or insoluble in water. In certain embodiments of the present invention, the active ingredient is added to the soft-chew tablet composition by dry blending. In certain embodiments of the present invention, the active ingredient may be conjugated with other ingredients, such as cyclodextrins, surfactants, solubility or bioavailability enhancers, etc., to inhibit interactions with other excipients or with the environment, or to promote the chemical stability, improve solubility, enhance bioavailability, or improve the palatability of the nutritional ingredient or pharmaceutically active agent. Similarly, the pharmaceutically active ingredient may be incorporated into a novel drug delivery system, such as microspheres, microcapsules, liposomes, niosomes, nanoparticles, microemulsions, or nanoemulsions to protect the drug or permit organ targeting. In certain embodiments of the present invention, the rate of release of the active ingredient may be modulated or controlled by, for example, the use of controlled or sustained release agents (e.g., polymers) or by using excipients (e.g., disintegrants) that promote in rapid release, as appropriate.

In certain preferred embodiments, as provided in the Examples included hereinbelow, the soft-chew tablets formed by the inventive process exhibit a hardness of less than 2 kp when measured on a tablet hardness tester. In certain preferred embodiments, as provided in the Examples included hereinbelow, the soft-chew tablets formed by the inventive process exhibit a hardness of less than 1 kp when measured on a tablet hardness tester. In certain preferred embodiments, as provided in the Examples included hereinbelow, the soft-chew tablets formed by the inventive process exhibit no hardness when measured on a tablet hardness tester.

The measure of the mechanical integrity of tablets is their breaking force or hardness, which is the force required to cause them to fail (i.e., break) in a specific plane. Various equipment is used for hardness measurements, for example a Monsanto Hardness Tester, Stokes Hardness tester, Pfizer Hardness Tester, Strong-Cobb Hardness Tester, or Schleuniger Hardness tester. Tablet hardness can be expressed using various units depending on the equipment used for hardness measurement. Typical units for tablet hardness measurement are newtons, pounds, Strong-Cobb units, and kiloponds. In the Examples included hereinbelow, a Schleuniger Hardness tester was used, and the value for hardness was provided in kiloponds or newtons. This apparatus has two parallel platens between which a tablet is placed. A load is applied and the value of the hardness is measured. The platen faces are polished smooth and precision-ground perpendicularly to the direction of movement. Perpendicularity is preserved during platen movement, and the mechanism is free of any bending or torsion displacements as the load is applied. The contact faces are larger than the area of contact with the tablet.

As tablet hardness decreases, tablet friability generally increases. But the inventors hereof have unexpectedly found that for the formulations described herein, soft-chew tablets with hardness values of less than 2 kp, or lower, tablet friability remains less than 1%. In certain preferred embodiments, as provided in the Examples included hereinbelow, the soft-chew tablets formed by the inventive process exhibit a friability of less than about 1%, when measured in accordance with the USP friability test. In certain preferred embodiments, as provided in the Examples included hereinbelow, the soft-chew tablets formed by the inventive process exhibit a friability of less than about 0.5%, when measured in accordance with the USP friability test. In certain preferred embodiments, as provided in the Examples included hereinbelow, the soft-chew tablets formed by the inventive process exhibit a friability of less than about 0.5%, when measured in accordance with the USP friability test. In certain preferred embodiments, as provided in the Examples included hereinbelow, the soft-chew tablets formed by the inventive process exhibit a friability of less than about 0.1% at 100-rotations (in accordance with the USP friability test), 200-rotations, and even 300-rotations.

The soft-chew tablets formed by the inventive process, as provided in the Examples included hereinbelow, maintain a characteristic selected from chewiness, hardness, compression energy, adhesion, cohesiveness, springiness, and modulus, and any combination of any two or more thereof (when measured by the texture analyzer as described in the Examples included hereinbelow) sufficient to provide a chewable texture.

In certain preferred embodiments, the soft-chew tablets of the present invention have a weight (i.e., mass) between about 0.1 g and about 10 g. In certain embodiments, the soft-chew tablet of the present invention has a weight between about 0.5 g and about 4.0 g. In certain embodiments, the soft-chew tablet of the present invention has a weight between about 0.1 g and about 3.0 g. In certain embodiments, the soft-chew tablet of the present invention has a weight of about 0.1 g and about 2.0 g. In certain embodiments of the present invention, the weight of the soft-chew tablet can be between about 0.1 g and about 1.0 g; between about 1.1 g and about 2.0 g; between about 2.1 g and about 3.0 g; between about 3.0 g and 3.1 g and about 4.0 g; or between about 4.1 g and about 5.0 g.

The soft-chew tablets of the present invention may have a wide range of weights, dimensions, and shapes to adapt to the need of the target patient population.

The soft-chew tablets of the present invention can be packaged in bulk primary packaging, or as singular unit primary packaging.

Certain aspects of the present invention relate to a tablet compression tooling that provides an anti-sticking means for tablet formulations that are sticky and/or necessarily moist, such as lubricated granules. In certain embodiments of the present invention, the tablet compression tool assembly includes an upper punch, a lower punch, and a die.

In certain embodiments of the present invention, a tablet compression tool assembly includes upper and lower punches. The punches include a head, a neck, a body, a stem, and a tip. The head includes a head flat, a head diameter, an outer head radius, and an under head angle. The neck is arranged adjacent the head and extends axially toward the body of the punch. The body typically includes one or more keyways to facilitate arrangement of the punch on the tablet compressing device. The stem projects axially from the punch body to the tip. The tip includes a face and a cup depth. The punches may also include projections on the tip face to facilitate debossing numbers, letters, break lines, logos, and other designs into the surface of the tablet.

In certain embodiments of the present invention, the die includes die faces spaced-apart by a die body, an outer die radius, a die bore, and a bore insert.

In certain preferred embodiments of the present invention, the punch tips and bore insert are formed from a material having the following characteristics: low friction, self-cleaning, durable, resistant to a wide range of temperatures, non-flammable, corrosion resistant, and/or providing suitable electrical resistance. For instance, in certain embodiments of the present invention, the punch tips and bore insert are made from PTFE. Suitable PTFE materials are marketed under the brand name Teflon®.

In other embodiments of the present invention, the punch tips and bore insert are made from POM, which is a high-performance acetal resin with several suitable physical and mechanical properties. POM is a highly-crystalline engineered thermoplastic that is widely regarded for its durability, stiffness, and exceptional dimensional stability. Suitable POM materials are marketed under the brand name Delrin®.

POM sheet and rods come in many forms, filled and unfilled. In certain embodiments of the present invention, the punch tips and bore insert are made from PTFE-filled copolymer Delrin, which provides outstanding durability. Often this copolymer material is used in the place of machined metal and plastics when good dimensional stability, minimal friction, and excellent resistance to wear are required. The PTFE-filled copolymer Delrin may be utilized under the present invention without any form of grease or lubricant. The white PTFE-filled copolymer Delrin complies with industry rules and regulations, such as those of the FDA.

Additional advantages of the various embodiments will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments but is not necessarily included. Thus, the present disclosure encompasses a variety of combinations and/or integrations of the specific embodiments described herein.

EXAMPLES

The following examples set forth preferred embodiments in accordance with the invention. It is to be understood, however, that these examples are provided by way of illustration, and nothing therein should be taken as a limitation upon the overall scope of the invention.

Example 1: A process for making soft-chew tablets in accordance with certain aspects of the present invention is provided in Example 1 below. The ingredients corresponding to Example 1 are tabulated in Table 1 with the amount of each ingredient used in the process (i.e., the batch quantity) given in percent-by-weight (% w/w) and in milligrams. In Example 1, the active ingredient is simethicone. Each soft-chew tablet formed by the process of Example 1 has an active strength of simethicone of about three hundred ninety-nine milligrams (399 mg). The amount of each ingredient provided in Table 1 corresponds to the formation of a single soft-chew tablet; however, as should be understood by those having ordinary skill in the art, the principles of Example 1 can be used to make more soft-chew tablets by proportionally increasing the amount of the ingredients as necessary to produce the desired quantity of soft-chew tablets.

TABLE 1

| Ingredient Name | Amount Per Unit (mg) | % w/w |
| --- | --- | --- |
| Carnauba wax | 60.000 | 2.857% |
| Citric acid anhydrous | 13.000 | 0.619% |
| Color agent (FD&C red) | 2.500 | 0.119% |
| Corn oil | 60.000 | 2.857% |
| Croscarmellose sodium | 50.000 | 2.381% |
| Crospovidone | 50.000 | 2.381% |
| Dried glucose syrup | 270.000 | 12.857% |
| Flavor agent (mixed berry) | 22.000 | 1.048% |
| Glycerin | 275.000 | 13.095% |
| Maltitol solution | 160.000 | 7.619% |
| Mannitol | 273.880 | 13.042% |
| Milk powder | 233.000 | 11.095% |
| Partially pregelatinized starch | 170.000 | 8.095% |
| Simethicone (powder) | 399.420 | 19.020% |
| Sucralose | 1.200 | 0.057% |
| Sugar (fine) | 60.000 | 2.857% |
| TOTAL | 2100.000 | 100.000% |

Procedure—Example 1

Step 1: The batch quantities of crospovidone, croscarmellose sodium, dried glucose syrup, and simethicone, along with, about 82% of the batch quantity of partially pregelatinized starch, 74% of the batch quantity of mannitol, and 70% of the batch quantity of milk powder were co-sifted with a No. 30 American Standard Test Sieve Series (ASTM).

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with about 69% of the batch quantity of citric acid anhydrous and 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of sucralose along with the remaining batch quantities of citric acid anhydrous and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of corn oil was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3-millimeter (3 mm) screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a square-shaped (approx. 15.3 mm by 15.3 mm) polytetrafluoroethylene ("PTFE") punch, having the number "7" embossed on one side, to form a compressed tablet.

Step 18: The tablets from Step 17 were coated using the batch quantity of sugar.

Example 2: A process for making soft-chew tablets in accordance with certain aspects of the present invention is provided in Example 2 below. The ingredients corresponding to Example 2 are tabulated in Table 2 with the amount of each ingredient used in the process (i.e., the batch quantity) given in percent-by-weight (% w/w) and in milligrams. In Example 2, the active ingredient is simethicone. Each soft-chew tablet formed by the process of Example 2 has an active strength of simethicone of about 264 mg. The amount of each ingredient provided in Table 2 corresponds to the formation of a single soft-chew tablet; however, as should be understood by those having ordinary skill in the art, the principles of Example 2 can be used to make more soft-chew tablets by proportionally increasing the amount of the ingredients as necessary to produce the desired quantity of soft-chew tablets.

TABLE 2

| Ingredient Name | Amount Per Unit (mg) | % w/w |
|---|---|---|
| Carnauba wax | 95.000 | 4.872% |
| Citric acid anhydrous | 10.500 | 0.538% |
| Color agent (FD&C red) | 2.650 | 0.136% |
| Croscarmellose sodium | 53.000 | 2.718% |
| Crospovidone | 53.000 | 2.718% |
| Dried glucose syrup | 321.530 | 16.489% |
| Flavor agent (mixed berry) | 23.200 | 1.190% |
| Glycerin | 137.000 | 7.026% |
| Maltitol solution | 147.000 | 7.538% |
| Mannitol | 253.000 | 12.974% |
| Milk powder | 273.000 | 14.000% |
| Partially pregelatinized starch | 158.000 | 8.103% |
| Simethicone (liquid) | 263.850 | 13.531% |
| Sorbitol (powder) | 105.000 | 5.385% |
| Sucralose | 1.270 | 0.065% |
| Sugar (fine) | 53.000 | 2.718% |
| TOTAL | 1950.000 | 100.000% |

Procedure—Example 2

Step 1: The batch quantities of croscarmellose sodium, dried glucose syrup, and, sorbitol (powder) along with, about 80% of the batch quantity of partially pregelatinized starch, 77% of the batch quantity of milk powder, and 75% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone, 70% of the batch quantity of citric acid anhydrous and 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 40 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of sucralose along with the remaining batch quantities of citric acid anhydrous and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 5 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a square-shaped (approx. 15.3 mm by 15.3 mm) PTFE punch, having the number "7" embossed on one side, to form a compressed tablet.

Step 18: The tablets from Step 17 were coated using the batch quantity of sugar.

Example 3: A process for making soft-chew tablets in accordance with certain aspects of the present invention is provided in Example 3 below. The ingredients corresponding to Example 3 are tabulated in Table 3 with the amount of each ingredient used in the process (i.e., the batch quantity) given in percent-by-weight (% w/w) and in milligrams. In Example 3, the active ingredient is simethicone. Each soft-chew tablet formed by the process of Example 3 has an active strength of simethicone of about 264 mg. The amount of each ingredient provided in Table 3 corresponds to the formation of a single soft-chew tablet; however, as should be understood by those having ordinary skill in the art, the principles of Example 3 can be used to make more soft-chew tablets by proportionally increasing the amount of the ingredients as necessary to produce the desired quantity of soft-chew tablets.

TABLE 3

| Ingredient Name | Amount Per Unit (mg) | % w/w |
|---|---|---|
| Carnauba wax | 95.000 | 4.872% |
| Citric acid anhydrous | 10.500 | 0.538% |
| Color agent (FD&C red) | 2.650 | 0.136% |
| Croscarmellose sodium | 53.000 | 2.718% |
| Crospovidone | 53.000 | 2.718% |
| Dried glucose syrup | 321.530 | 16.489% |
| Flavor agent (mixed berry) | 23.200 | 1.190% |
| Glycerin | 137.000 | 7.026% |
| Maltitol solution | 147.000 | 7.538% |
| Mannitol | 253.000 | 12.974% |
| Milk powder | 273.000 | 14.000% |
| Partially pregelatinized starch | 158.000 | 8.103% |
| Simethicone | 263.850 | 13.531% |
| Sorbitol (powder) | 105.000 | 5.385% |
| Sucralose | 1.270 | 0.065% |
| Sugar (fine caster) | 53.000 | 2.718% |
| TOTAL | 1950.000 | 100.000% |

Procedure—Example 3

Step 1: The batch quantities of croscarmellose sodium, dried glucose syrup, and, sorbitol (powder) along with, about 80% of the batch quantity of partially pregelatinized starch, 77% of the batch quantity of milk powder, and 75% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone, 70% of the batch quantity of citric acid anhydrous and 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 40 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of sucralose along with the remaining batch quantities of citric acid anhydrous and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 5 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a square-shaped (approx. 15.3 mm by 15.3 mm) PTFE punch, having the number "7" embossed on one side, to form a compressed tablet.

Step 18: The tablets from Step 17 were coated using the batch quantity of sugar.

Example 4: A process for making soft-chew tablets in accordance with certain aspects of the present invention is provided in Example 4 below. The ingredients corresponding to Example 4 are tabulated in Table 4 with the amount of each ingredient used in the process (i.e., the batch quantity) given in percent-by-weight (% w/w) and in milligrams. In Example 4, the active ingredient is simethicone. Each soft-chew tablet formed by the process of Example 4 has an active strength of simethicone of about 264 mg. The amount of each ingredient provided in Table 4 corresponds to the formation of a single soft-chew tablet; however, as should be understood by those having ordinary skill in the art, the principles of Example 4 can be used to make more soft-chew tablets by proportionally increasing the amount of the ingredients as necessary to produce the desired quantity of soft-chew tablets.

TABLE 4

| Ingredient Name | Amount Per Unit (mg) | % w/w |
| --- | --- | --- |
| Carnauba wax | 95.000 | 4.872% |
| Citric acid anhydrous | 10.500 | 0.538% |
| Color agent (FD&C red) | 2.650 | 0.136% |
| Croscarmellose sodium | 53.000 | 2.718% |
| Crospovidone | 53.000 | 2.718% |
| Flavor agent (mixed berry) | 23.200 | 1.190% |
| Glycerin | 137.000 | 7.026% |
| Maltitol solution | 147.000 | 7.538% |
| Maltodextrin | 321.530 | 16.489% |
| Mannitol | 253.000 | 12.974% |
| Milk powder | 273.000 | 14.000% |
| Partially pregelatinized starch | 158.000 | 8.103% |
| Simethicone | 263.850 | 13.531% |
| Sorbitol (powder) | 105.000 | 5.385% |
| Sucralose | 1.270 | 0.065% |
| Sugar (fine caster) | 53.000 | 2.718% |
| TOTAL | 1950.000 | 100.000% |

Procedure—Example 4

Step 1: The batch quantities of croscarmellose sodium, maltodextrin, and sorbitol (powder) along with, about 80% of the batch quantity of partially pregelatinized starch, 77% of the batch quantity of milk powder, and 75% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone, 70% of the batch quantity of citric acid anhydrous and 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 40 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of sucralose along with the remaining batch quantities of citric acid anhydrous and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 5 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a square-shaped (approx. 15.3 mm by 15.3 mm) PTFE punch, having the number "7" embossed on one side, to form a compressed tablet.

Step 18: The tablets from Step 17 were coated using the batch quantity of sugar.

Example 5: A process for making soft-chew tablets in accordance with certain aspects of the present invention is provided in Example 5 below. The ingredients corresponding to Example 5 are tabulated in Table 5 with the amount of each ingredient used in the process (i.e., the batch quantity) given in percent-by-weight (% w/w) and in milligrams. In Example 5, the active ingredient is simethicone. Each soft-chew tablet formed by the process of Example 5 has an active strength of simethicone of about 264 mg. The amount of each ingredient provided in Table 5 corresponds to the formation of a single soft-chew tablet; however, as should be understood by those having ordinary skill in the art, the principles of Example 5 can be used to make more soft-chew tablets by proportionally increasing the amount of the ingredients as necessary to produce the desired quantity of soft-chew tablets.

TABLE 5

| Ingredient Name | Amount Per Unit (mg) | % w/w |
|---|---|---|
| Carnauba wax | 95.000 | 4.872% |
| Citric acid anhydrous | 10.500 | 0.538% |
| Color agent (FD&C red) | 2.650 | 0.136% |
| Croscarmellose sodium | 53.000 | 2.718% |
| Crospovidone | 53.000 | 2.718% |
| Dextrose anhydrous | 321.530 | 16.489% |
| Flavor agent (mixed berry) | 23.200 | 1.190% |
| Glycerin | 137.000 | 7.026% |
| Maltitol solution | 147.000 | 7.538% |
| Mannitol | 253.000 | 12.974% |
| Milk powder | 273.000 | 14.000% |
| Partially pregelatinized starch | 158.000 | 8.103% |
| Simethicone | 263.850 | 13.531% |
| Sorbitol (powder) | 105.000 | 5.385% |
| Sucralose | 1.270 | 0.065% |
| Sugar (fine caster) | 53.000 | 2.718% |
| TOTAL | 1950.000 | 100.000% |

Procedure—Example 5

Step 1: The batch quantities of croscarmellose sodium, dextrose anhydrous, and sorbitol (powder) along with, about 80% of the batch quantity of partially pregelatinized starch, 77% of the batch quantity of milk powder, and 75% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone, 70% of the batch quantity of citric acid anhydrous and 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 40 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of sucralose along with the remaining batch quantities of citric acid anhydrous and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 5 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a square-shaped (approx. 15.3 mm by 15.3 mm) PTFE punch, having the number "7" embossed on one side, to form a compressed tablet.

Step 18: The tablets from Step 17 were coated using the batch quantity of sugar.

Example 6: A process for making soft-chew tablets in accordance with certain aspects of the present invention is provided in Example 6 below. The ingredients corresponding to Example 6 are tabulated in Table 6 with the amount of each ingredient used in the process (i.e., the batch quantity) given in percent-by-weight (% w/w) and in milligrams. In Example 6, the active ingredient is simethicone.

Each soft-chew tablet formed by the process of Example 6 has an active strength of simethicone of about 264 mg. The amount of each ingredient provided in Table 6 corresponds to the formation of a single soft-chew tablet; however, as should be understood by those having ordinary skill in the art, the principles of Example 6 can be used to make more soft-chew tablets by proportionally increasing the amount of the ingredients as necessary to produce the desired quantity of soft-chew tablets.

TABLE 6

| Ingredient Name | Amount Per Unit (mg) | % w/w |
|---|---|---|
| Carnauba wax | 95.000 | 4.872% |
| Citric acid anhydrous | 10.500 | 0.538% |
| Color agent (FD&C red) | 2.650 | 0.136% |
| Croscarmellose sodium | 53.000 | 2.718% |
| Crospovidone | 53.000 | 2.718% |
| Dried glucose syrup (Dextrose Equivalent 47) | 321.530 | 16.489% |
| Flavor agent (mixed berry) | 23.200 | 1.190% |
| Glycerin | 137.000 | 7.026% |
| Maltitol solution | 147.000 | 7.538% |
| Mannitol | 253.000 | 12.974% |
| Milk powder | 273.000 | 14.000% |
| Partially pregelatinized starch | 158.000 | 8.103% |
| Simethicone | 263.850 | 13.531% |
| Sorbitol (powder) | 105.000 | 5.385% |
| Sucralose | 1.270 | 0.065% |
| Sugar (fine caster) | 53.000 | 2.718% |
| TOTAL | 1950.000 | 100.000% |

Procedure—Example 6

Step 1: The batch quantities of croscarmellose sodium, dried glucose syrup (Dextrose Equivalent 47), and sorbitol (powder) along with, about 80% of the batch quantity of partially pregelatinized starch, 77% of the batch quantity of milk powder, and 75% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone, 70% of the batch quantity of citric acid anhydrous and 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 40 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of sucralose along with the remaining batch quantities of citric acid anhydrous and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 5 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a square-shaped (approx. 15.3 mm by 15.3 mm) PTFE punch, having the number "7" embossed on one side, to form a compressed tablet.

Step 18: The tablets from Step 17 were coated using the batch quantity of sugar.

Example 7: A process for making soft-chew tablets in accordance with certain aspects of the present invention is provided in Example 7 below. The ingredients corresponding to Example 7 are tabulated in Table 7 with the amount of each ingredient used in the process (i.e., the batch quantity) given in percent-by-weight (% w/w) and in milligrams. In Example 7, the active ingredient is simethicone. Each soft-chew tablet formed by the process of Example 7 has an active strength of simethicone of about 264 mg. The amount of each ingredient provided in Table 7 corresponds to the formation of a single soft-chew tablet; however, as should be understood by those having ordinary skill in the art, the principles of Example 7 can be used to make more soft-chew tablets by proportionally increasing the amount of the ingredients as necessary to produce the desired quantity of soft-chew tablets.

TABLE 7

| Ingredient Name | Amount Per Unit (mg) | % w/w |
|---|---|---|
| Carnauba wax | 95.000 | 4.872% |
| Citric acid anhydrous | 10.500 | 0.538% |
| Color agent (FD&C red) | 2.650 | 0.136% |
| Croscarmellose sodium | 53.000 | 2.718% |
| Crospovidone | 53.000 | 2.718% |
| Dried glucose syrup (Dextrose Equivalent 30) | 321.530 | 16.489% |
| Flavor agent (mixed berry) | 23.200 | 1.190% |
| Glycerin | 137.000 | 7.026% |
| Maltitol solution | 147.000 | 7.538% |
| Mannitol | 253.000 | 12.974% |
| Milk powder | 273.000 | 14.000% |
| Partially pregelatinized starch | 158.000 | 8.103% |
| Simethicone | 263.850 | 13.531% |
| Sorbitol (powder) | 105.000 | 5.385% |

TABLE 7-continued

| Ingredient Name | Amount Per Unit (mg) | % w/w |
|---|---|---|
| Sucralose | 1.270 | 0.065% |
| Sugar (fine caster) | 53.000 | 2.718% |
| TOTAL | 1950.000 | 100.000% |

Procedure—Example 7

Step 1: The batch quantities of croscarmellose sodium, dried glucose syrup (Dextrose Equivalent 30), and sorbitol (powder) along with, about 80% of the batch quantity of partially pregelatinized starch, 77% of the batch quantity of milk powder, and 75% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone, 70% of the batch quantity of citric acid anhydrous and 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 40 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of sucralose along with the remaining batch quantities of citric acid anhydrous and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 5 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a square-shaped (approx. 15.3 mm by 15.3 mm) PTFE punch, having the number "7" embossed on one side, to form a compressed tablet.

Step 18: The tablets from Step 17 were coated using the batch quantity of sugar.

Example 8: A process for making soft-chew tablets in accordance with certain aspects of the present invention is provided in Example 8 below. The ingredients corresponding to Example 8 are tabulated in Table 8 with the amount of each ingredient used in the process (i.e., the batch quantity) given in percent-by-weight (% w/w) and in milligrams. In Example 8, the active ingredient is simethicone. Each soft-chew tablet formed by the process of Example 8 has an active strength of simethicone of about 264 mg. The amount of each ingredient provided in Table 8 corresponds to the formation of a single soft-chew tablet; however, as should be understood by those having ordinary skill in the art, the principles of Example 8 can be used to make more soft-chew tablets by proportionally increasing the amount of the ingredients as necessary to produce the desired quantity of soft-chew tablets.

TABLE 8

| Ingredient Name | Amount Per Unit (mg) | % w/w |
|---|---|---|
| Carnauba wax | 95.000 | 4.872% |
| Citric acid anhydrous | 10.500 | 0.538% |
| Color agent (FD&C red) | 2.650 | 0.136% |
| Croscarmellose sodium | 53.000 | 2.718% |
| Crospovidone | 53.000 | 2.718% |
| Dried glucose syrup (Dextrose Equivalent 12) | 321.530 | 16.489% |
| Flavor agent (mixed berry) | 23.200 | 1.190% |
| Glycerin | 137.000 | 7.026% |
| Maltitol solution | 147.000 | 7.538% |
| Mannitol | 253.000 | 12.974% |
| Milk powder | 273.000 | 14.000% |
| Partially pregelatinized starch | 158.000 | 8.103% |
| Simethicone | 263.850 | 13.531% |
| Sorbitol (powder) | 105.000 | 5.385% |
| Sucralose | 1.270 | 0.065% |
| Sugar (fine caster) | 53.000 | 2.718% |
| TOTAL | 1950.000 | 100.000% |

Procedure—Example 8

Step 1: The batch quantities of croscarmellose sodium, dried glucose syrup (Dextrose Equivalent 12), and sorbitol (powder) along with, about 80% of the batch quantity of partially pregelatinized starch, 77% of the batch quantity of milk powder, and 75% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone, 70% of the batch quantity of citric acid anhydrous and 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 40 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of sucralose along with the remaining batch quantities of citric acid anhydrous and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 5 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a square-shaped (approx. 15.3 mm by 15.3 mm) PTFE punch, having the number "7" embossed on one side, to form a compressed tablet.

Step 18: The tablets from Step 17 were coated using the batch quantity of sugar.

Example 9: A process for making soft-chew tablets in accordance with certain aspects of the present invention is provided in Example 9 below. The ingredients corresponding to Example 9 are tabulated in Table 9 with the amount of each ingredient used in the process (i.e., the batch quantity) given in percent-by-weight (% w/w) and in milligrams. In Example 9, the active ingredients are dextromethorphan HBr and doxylamine succinate. Each soft-chew tablet formed by the process of Example 9 has an active strength of dextromethorphan HBr of approximately 30 mg and an active strength of doxylamine succinate of about 12.5 mg. The amount of each ingredient provided in Table 9 corresponds to the formation of a single soft-chew tablet; however, as should be understood by those having ordinary skill in the art, the principles of Example 9 can be used to make more soft-chew tablets by proportionally increasing the amount of the ingredients as necessary to produce the desired quantity of soft-chew tablets.

TABLE 9

| Ingredient Name | Amount Per Unit (mg) | % w/w |
|---|---|---|
| Calcium gluconate monohydrate | 25.000 | 0.893% |
| Carnauba wax | 60.000 | 2.143% |
| Citric acid anhydrous | 15.000 | 0.536% |
| Coconut oil | 100.000 | 3.571% |
| Color agent (FD&C red) | 3.000 | 0.107% |
| Croscarmellose sodium | 50.000 | 1.786% |
| Crospovidone | 150.000 | 5.357% |
| Dextromethorphan HBr drug complex | 90.000 | 3.214% |
| Doxylamine Succinate drug complex | 37.500 | 1.339% |
| Dried glucose syrup | 400.000 | 14.286% |
| Flavor agent (mixed berry) | 30.000 | 1.071% |
| Hydroxypropyl beta-cyclodextrin | 100.000 | 3.571% |
| Maltitol solution | 120.000 | 4.286% |
| Mannitol | 50.000 | 1.786% |
| Milk powder | 300.000 | 10.714% |
| Non crystallizing sorbitol solution | 500.000 | 17.857% |
| Partially pregelatinized starch | 100.000 | 3.571% |
| Silicified microcrystalline cellulose | 116.500 | 4.161% |
| Sorbitol (powder) | 450.000 | 16.071% |
| Sucralose | 3.000 | 0.107% |
| Sugar (fine) | 100.000 | 3.571% |
| TOTAL | 2800.000 | 100.000% |

Procedure—Example 9

Step 1: The batch quantities of calcium gluconate monohydrate, dextromethorphan HBr drug complex, and doxylamine succinate drug complex were co-sifted with a No. 30 ASTM.

Step 2: The sifted ingredients of Step 1 were sifted a second time with a No. 30 ASTM and collected in a polybag.

Step 3: The batch quantities of dried glucose syrup, hydroxypropyl beta-cyclodextrin, milk powder, silicified microcrystalline cellulose; along with, about 67% of the batch quantity of sorbitol (powder), 50% of the batch quantity of croscarmellose sodium, 50% of the batch quantity of crospovidone, and the material of Step 2 were co-sifted with a No. 30 ASTM.

Step 4: The sifted ingredients of Step 3 were sifted a second time with a No. 30 ASTM to form an intragranular ingredient mixture, which was collected in a polybag.

Step 5: The remaining batch quantities of croscarmellose sodium, crospovidone, and sorbitol (powder) along with the batch quantity of mannitol, the batch quantity partially pregelatinized starch, and about 67% of the batch quantity of flavor agent were co-sifted with a No. 30 ASTM.

Step 6: The sifted ingredients of Step 5 were sifted a second time with a No. 30 ASTM to form an extragranular ingredient mixture, which was collected in a polybag.

Step 7: The batch quantity of carnauba wax was sifted using a No. 60 ASTM and collected in a polybag.

Step 8: The batch quantity of maltitol solution was added to the batch quantity of non crystallizing sorbitol solution under continuous stirring.

Step 9: The batch quantity of color agent was added to the mixture of Step 8 under continuous stirring.

Step 10: The batch quantities of sucralose and citric acid anhydrous along with the remaining batch quantity of flavor agent were added to the mixture of Step 9 under continuous stirring.

Step 11: The mixture of Step 10 was stirred until a uniform granulation dispersion was formed.

Step 12: The intragranular ingredient mixture of Step 4 was transferred to a rapid mixer granulator (with the impeller set to a slow speed and the chopper off) and mixed for approximately 10 minutes.

Step 13: The batch quantity of coconut oil was slowly added to the mixture of Step 12 in a thin stream under continuous mixing (with the impeller set to a slow speed and the chopper on) with intermittent racking.

Step 14: The uniform granulation dispersion of Step 11 was slowly added to the mixture of Step 13 in a thin stream under continuous mixing (with the impeller set to a slow speed and the chopper on) with intermittent racking to form a wet mass.

Step 15: The wet mass of Step 14 and approximately 75% of the extragranular ingredient mixture of Step 6 were passed through a cone mill to form milled granules. The cone mill was fitted with a 4 mm screen, the knife was in the forward position, and the speed setting was slow.

Step 16: The milled granules of Step 15 along with the remaining extragranular ingredient mixture of Step 6 were co-sifted with a No. 8 ASTM to form granules. The granules were collected in a double-lined polybag.

Step 17: The granules of Step 16 were sifted a second time with a No. 8 ASTM and collected in a double-lined polybag.

Step 18: The granules of Step 17 were lubricated using the carnauba wax of Step 7 for approximately 2-minutes.

Step 19: The granules from Step 18 were compressed using a rotary tablet press equipped with a round-shaped (diameter of approx. 20 mm) PTFE punch to form a compressed tablet.

Step 20: The tablets from Step 19 were coated using the batch quantity of sugar.

Example 10: A process for making soft-chew tablets in accordance with certain aspects of the present invention is provided in Example 10 below. The ingredients corresponding to Example 10 are tabulated in Table 10 with the amount of each ingredient used in the process (i.e., the batch quantity) given in percent-by-weight (% w/w) and in milligrams. In Example 10, the active ingredient is acetaminophen. Each soft-chew tablet formed by the process of Example 10 has an active strength of acetaminophen of about 339 mg. The amount of each ingredient provided in Table 10 corresponds to the formation of a single soft-chew tablet; however, as should be understood by those having ordinary skill in the art, the principles of Example 10 can be used to necessary to produce the desired quantity of soft-chew tablets.

TABLE 10

| Ingredient Name | Amount Per Unit (mg) | % w/w |
| --- | --- | --- |
| Acetaminophen | 338.880 | 8.918% |
| Calcium gluconate monohydrate | 50.000 | 1.316% |
| Carnauba wax | 145.000 | 3.816% |
| Citric acid anhydrous | 30.000 | 0.789% |
| Color agent (FD&C red) | 4.750 | 0.125% |
| Croscarmellose sodium | 85.000 | 2.237% |
| Crospovidone | 85.000 | 2.237% |
| Dried glucose syrup | 600.000 | 15.789% |
| Flavor agent (mixed berry) | 55.000 | 1.447% |
| Glycerin | 440.000 | 11.579% |
| Maltitol solution | 450.000 | 11.842% |
| Mannitol | 417.370 | 10.983% |
| Milk powder | 470.000 | 12.368% |
| Partially pregelatinized starch | 250.000 | 6.579% |
| Simethicone | 100.000 | 2.632% |
| Sorbitol (powder) | 170.000 | 4.474% |
| Sucralose | 9.000 | 0.237% |
| Sugar (fine) | 100.000 | 2.632% |
| TOTAL | 3800.000 | 100.000% |

Procedure—Example 10

Step 1: The batch quantities of acetaminophen and calcium gluconate monohydrate were co-sifted with a No. 30 ASTM and collected in a polybag.

Step 2: The material of Step 1 was sifted a second time with a No. 30 ASTM and collected in a polybag.

Step 3: Approximately 83% of the batch quantity of carnauba wax was co-sifted with the material of Step 2 with a No. 30 ASTM and collected in a polybag.

Step 4: The material of Step 3 and the batch quantities of croscarmellose sodium, dried glucose syrup, sorbitol (powder); along with, 69% of the batch quantity of mannitol, 68% of the batch quantity of milk powder, and 80% of the batch quantity of partially pregelatinized starch were co-sifted with a No. 30 ASTM and collected in a polybag.

Step 5: The sifted ingredients of Step 4 were sifted a second time with a No. 30 ASTM to form an intragranular ingredient mixture, which was collected in a polybag.

Step 6: The remaining batch quantities of mannitol, milk powder, and partially pregelatinized starch along with the batch quantity of crospovidone and about 55% of the batch quantity of flavor agent were co-sifted with a No. 30 ASTM.

Step 7: The sifted ingredients of Step 6 were sifted a second time with a No. 30 ASTM to form an extragranular ingredient mixture, which was collected in a polybag.

Step 8: The remaining batch quantity of carnauba wax was sifted using a No. 60 ASTM and collected in a polybag.

Step 9: The batch quantity of maltitol solution was added to the batch quantity of glycerin under continuous stirring.

Step 10: The batch quantity of color agent was added to the mixture of Step 9 under continuous stirring.

Step 11: The batch quantities of sucralose and citric acid anhydrous along with the remaining batch quantity of flavor agent were added to the mixture of Step 10 under continuous stirring.

Step 12: The mixture of Step 11 was stirred until a uniform granulation dispersion was formed.

Step 13: The intragranular ingredient mixture of Step 5 was transferred to a rapid mixer granulator (with the impeller set to a slow speed and the chopper off) and mixed for approximately 10 minutes.

Step 14: The batch quantity of simethicone was slowly added to the mixture of Step 13 in a thin stream under continuous mixing (with the impeller set to a slow speed and the chopper on) with intermittent racking.

Step 15: The uniform granulation dispersion of Step 12 was slowly added to the mixture of Step 14 in a thin stream under continuous mixing (with the impeller set to a slow speed and the chopper on) with intermittent racking to form a wet mass.

Step 16: The wet mass of Step 15 and approximately 75% of the extragranular ingredient mixture of Step 7 were passed through a cone mill to form milled granules. The cone mill was fitted with a 4 mm screen, the knife was in the forward position, and the speed setting was slow.

Step 17: The milled granules of Step 16 along with the remaining extragranular ingredient mixture of Step 7 were co-sifted with a No. 8 ASTM to form granules. The granules were collected in a double-lined polybag.

Step 18: The granules of Step 17 were sifted a second time with a No. 8 ASTM and collected in a double-lined polybag.

Step 19: The granules of Step 18 were lubricated using the carnauba wax of Step 8 for approximately 2-minutes.

Step 20: The granules from Step 19 were compressed using a rotary tablet press equipped with a round-shaped (diameter of approx. 20 mm) PTFE punch, having "C1" embossed on one side, to form a compressed tablet.

Step 21: The tablets from Step 20 were coated using the batch quantity of sugar.

Example 11: A process for making soft-chew tablets in accordance with certain aspects of the present invention is provided in Example 11 below. The ingredients corresponding to Example 11 are tabulated in Table 11 with the amount of each ingredient used in the process (i.e., the batch quantity) given in percent-by-weight (% w/w) and in milligrams. In Example 11, the active ingredient is magnesium hydroxide. Each soft-chew tablet formed by the process of Example 11 has an active strength of magnesium hydroxide of about 1,233 mg. The amount of each ingredient provided in Table 11 corresponds to the formation of a single soft-chew tablet; however, as should be understood by those having ordinary skill in the art, the principles of Example 11 can be used to make more soft-chew tablets by proportionally increasing the amount of the ingredients as necessary to produce the desired quantity of soft-chew tablets.

TABLE 11

| Ingredient Name | Amount Per Unit (mg) | % w/w |
| --- | --- | --- |
| Carnauba wax | 30.000 | 0.769% |
| Color agent (FD&C red) | 5.000 | 0.128% |
| Croscarmellose sodium | 50.000 | 1.282% |
| Crospovidone | 50.000 | 1.282% |
| Dried glucose syrup | 488.000 | 12.513% |
| Flavor agent (mixed berry) | 60.000 | 1.538% |
| Glycerin | 850.000 | 21.795% |
| Liquid paraffin | 100.000 | 2.564% |
| Magnesium hydroxide | 1233.140 | 31.619% |
| Mannitol | 171.530 | 4.398% |
| Milk powder | 350.000 | 8.974% |
| Partially pregelatinized starch | 99.330 | 2.547% |
| Polyethylene glycol | 70.000 | 1.795% |
| Polyvinylpyrrolidone | 35.000 | 0.897% |
| Silicified microcrystalline cellulose | 50.000 | 1.282% |
| Sorbitol (powder) | 150.000 | 3.846% |
| Sucralose | 8.000 | 0.205% |
| Sugar (fine) | 100.000 | 2.564% |
| TOTAL | 3900.000 | 100.000% |

Procedure—Example 11

Step 1: The batch quantities of croscarmellose sodium, dried glucose syrup, magnesium hydroxide, partially pregelatinized starch, and sorbitol (powder) along with, about 71% of the batch quantity of milk powder and 42% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and milk powder, along with the batch quantity of crospovidone, the batch quantity of silicified microcrystalline cellulose, about 58% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantities of polyethylene glycol and polyvinylpyrrolidone were added to the batch quantity of glycerin under continuous stirring.

Step 7: The batch quantity of color agent was added to the mixture of Step 6 under continuous stirring.

Step 8: The batch quantity of sucralose along with the remaining batch quantity of flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of liquid paraffin was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 20 mm) PTFE punch, having "C1" embossed on one side, to form a compressed tablet.

Step 18: The tablets from Step 17 were coated using the batch quantity of sugar.

Example 12: A process for making soft-chew tablets in accordance with certain aspects of the present invention is provided in Example 12 below. The ingredients corresponding to Example 12 are tabulated in Table 12 with the amount of each ingredient used in the process (i.e., the batch quantity) given in percent-by-weight (% w/w) and in milligrams. In Example 12, the active ingredient is magnesium hydroxide. Each soft-chew tablet formed by the process of Example 12 has an active strength of magnesium hydroxide of about 1,233 mg. The amount of each ingredient provided in Table 12 corresponds to the formation of a single soft-chew tablet; however, as should be understood by those having ordinary skill in the art, the principles of Example 12 can be used to make more soft-chew tablets by proportionally increasing the amount of the ingredients as necessary to produce the desired quantity of soft-chew tablets.

TABLE 12

| Ingredient Name | Amount Per Unit (mg) | % w/w |
| --- | --- | --- |
| Carnauba wax | 30.000 | 0.769% |
| Color agent (FD&C red) | 5.000 | 0.128% |
| Croscarmellose sodium | 50.000 | 1.282% |

TABLE 12-continued

| Ingredient Name | Amount Per Unit (mg) | % w/w |
| --- | --- | --- |
| Crospovidone | 50.000 | 1.282% |
| Dried glucose syrup | 488.000 | 12.513% |
| Flavor agent (mixed berry) | 60.000 | 1.538% |
| Glycerin | 850.000 | 21.795% |
| Magnesium hydroxide | 1233.140 | 31.619% |
| Mannitol | 171.530 | 4.398% |
| Milk powder | 350.000 | 8.974% |
| Partially pregelatinized starch | 99.330 | 2.547% |
| Polyethylene glycol | 70.000 | 1.795% |
| Polyvinylpyrrolidone | 35.000 | 0.897% |
| Silicified microcrystalline cellulose | 50.000 | 1.282% |
| Simethicone | 100.000 | 2.564% |
| Sorbitol (powder) | 150.000 | 3.846% |
| Sucralose | 8.000 | 0.205% |
| Sugar (fine) | 100.000 | 2.564% |
| TOTAL | 3900.000 | 100.000% |

Procedure—Example 12

Step 1: The batch quantities of croscarmellose sodium, dried glucose syrup, magnesium hydroxide, partially pregelatinized starch, and sorbitol (powder) along with, about 71% of the batch quantity of milk powder and 42% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and milk powder, along with the batch quantity of crospovidone, the batch quantity of silicified microcrystalline cellulose, about 58% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantities of polyethylene glycol and polyvinylpyrrolidone were added to the batch quantity of glycerin under continuous stirring.

Step 7: The batch quantity of color agent was added to the mixture of Step 6 under continuous stirring.

Step 8: The batch quantity of sucralose along with the remaining batch quantity of flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 22 mm) PTFE punch, having "C1" embossed on one side, to form a compressed tablet.

Step 18: The tablets from Step 17 were coated using the batch quantity of sugar.

Example 13: A process for making soft-chew tablets in accordance with certain aspects of the present invention is provided in Example 13 below. The ingredients corresponding to Example 13 are tabulated in Table 13 with the amount of each ingredient used in the process (i.e., the batch quantity) given in percent-by-weight (% w/w) and in milligrams. In Example 13, the active ingredient is ibuprofen. Each soft-chew tablet formed by the process of Example 13 has an active strength of ibuprofen of about 243 mg. The amount of each ingredient provided in Table 13 corresponds to the formation of a single soft-chew tablet; however, as should be understood by those having ordinary skill in the art, the principles of Example 13 can be used to make more soft-chew tablets by proportionally increasing the amount of the ingredients as necessary to produce the desired quantity of soft-chew tablets.

TABLE 13

| Ingredient Name | Amount Per Unit (mg) | % w/w |
| --- | --- | --- |
| Advantol 300 | 434.500 | 16.396% |
| Carnauba wax | 50.000 | 1.887% |
| Color agent (FD&C blue) | 0.006 | 0.000% |
| Corn starch (granulated) | 238.420 | 8.997% |
| Dried glucose syrup | 313.210 | 11.819% |
| Flavor agent (icy mint) | 5.500 | 0.208% |
| Ibuprofen | 242.964 | 9.168% |
| Lecithin | 6.000 | 0.226% |
| Liquid paraffin | 72.000 | 2.717% |
| Magnesium stearate | 12.400 | 0.468% |
| Maltitol solution | 350.000 | 13.208% |
| Mannitol | 302.000 | 11.396% |
| Sorbitol (solution) | 336.000 | 12.679% |
| Sucralose | 2.000 | 0.075% |
| Sugar (extra fine caster) | 150.000 | 5.660% |
| Xylitol | 135.000 | 5.094% |
| TOTAL | 2650.000 | 100.000% |

Procedure—Example 13

Step 1: The batch quantities of carnauba wax, dried glucose syrup, flavor agent, and ibuprofen along with, about 90% of the batch quantity of corn starch (granulated), 77% of the batch quantity of mannitol, and 68% of the batch quantity of Advantol 300 were co-sifted with a No. ASTM.

Step 2: The sifted ingredients of Step 1 were sifted a second time with a No. 30 ASTM to form an intragranular ingredient mixture, which was collected in a polybag.

Step 3: The remaining batch quantities of Advantol 300, corn starch (granulated), and mannitol along with the batch quantity of xylitol were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of magnesium stearate was sifted using a No. 60 ASTM and collected in a polybag.

Step 6: The batch quantity of maltitol solution was added to the batch quantity of sorbitol (solution) under continuous stirring.

Step 7: The batch quantity of sucralose was added to the mixture of Step 6 under continuous stirring.

Step 8: The batch quantity of color agent was added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantities of lecithin and liquid paraffin were slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were lubricated using the magnesium stearate of Step 5 for approximately 2-minutes.

Step 16: The granules from Step 15 were compressed using a rotary tablet press equipped with a round-shaped (diameter of approx. 20 mm) punch to form a compressed tablet.

Step 17: The tablets from Step 16 were coated using the batch quantity of sugar.

Example 14: A process for making soft-chew tablets in accordance with certain aspects of the present invention is provided in Example 14 below. The ingredients corresponding to Example 14 are tabulated in Table 14 with the amount of each ingredient used in the process (i.e., the batch quantity) given in percent-by-weight (% w/w) and in milligrams. The amount of each ingredient provided in Table 14 corresponds to the formation of a single soft-chew tablet; however, as should be understood by those having ordinary skill in the art, the principles of Example 14 can be used to make more soft-chew tablets by proportionally increasing the amount of the ingredients as necessary to produce the desired quantity of soft-chew tablets.

TABLE 14

| Ingredient Name | Amount Per Unit (mg) | % w/w |
| --- | --- | --- |
| Carnauba wax | 100.000 | 3.774% |
| Color agent (yellow iron oxide) | 5.000 | 0.189% |

TABLE 14-continued

| Ingredient Name | Amount Per Unit (mg) | % w/w |
| --- | --- | --- |
| Corn oil | 50.000 | 1.887% |
| Flavor agent (honey) | 320.000 | 12.075% |
| Dried glucose syrup | 600.000 | 22.642% |
| Glycerin | 300.000 | 11.321% |
| Magnesium stearate | 10.500 | 0.396% |
| Mannitol | 572.200 | 21.592% |
| Milk powder | 350.000 | 13.208% |
| Partially pregelatinized starch | 190.500 | 7.189% |
| Sucralose | 1.800 | 0.068% |
| Sugar (fine caster) | 150.000 | 5.660% |
| TOTAL | 2650.000 | 100.000% |

Procedure—Example 14

Step 1: The batch quantity of dried glucose syrup along with, about 83% of the batch quantity of mannitol, 79% of the batch quantity of partially pregelatinized starch, and 71% of the batch quantity of milk powder were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with 6% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of magnesium stearate was sifted using a No. 60 ASTM and collected in a polybag.

Step 7: The remaining batch quantity of flavor agent was added to the batch quantity of glycerin under continuous stirring.

Step 8: The batch quantity of sucralose was added to the mixture of Step 7 under continuous stirring.

Step 9: The batch quantity of color agent was added to the mixture of Step 8 under continuous stirring.

Step 10: The mixture of Step 9 was stirred until a uniform granulation dispersion was formed.

Step 11: The intragranular ingredient mixture of Step 2 was transferred to a rapid mixer granulator (with the impeller set to a slow speed and the chopper off) and mixed for approximately 10 minutes.

Step 12: The batch quantity of corn oil was slowly added to the mixture of Step 11 in a thin stream under continuous mixing (with the impeller set to a slow speed and the chopper on) with intermittent racking.

Step 13: The uniform granulation dispersion of Step 10 was slowly added to the mixture of Step 12 in a thin stream under continuous mixing (with the impeller set to a slow speed and the chopper on) with intermittent racking to form a wet mass.

Step 14: The wet mass of Step 13 and approximately 60% to 80% of the extragranular ingredient mixture of Step 4 were passed through a cone mill to form milled granules. The cone mill was fitted with a 4 mm screen, the knife was in the forward position, and the speed setting was slow.

Step 15: The milled granules of Step 14 along with the remaining extragranular ingredient mixture of Step 4 were co-sifted with a No. 8 ASTM to form granules. The granules were collected in a double-lined polybag.

Step 16: The granules of Step 15 were pre-lubricated using the carnauba wax of Step 5 for approximately 2-minutes.

Step 17: The granules of Step 16 were lubricated using the magnesium stearate of Step 6 for approximately 2-minutes.

Step 18: The granules from Step 17 were compressed using a rotary tablet press equipped with a square-shaped (approx. 17 mm by 17 mm) punch to form a compressed tablet.

Step 19: The tablets from Step 18 were coated using the batch quantity of sugar.

Example 15: A process for making soft-chew tablets in accordance with certain aspects of the present invention is provided in Example 15 below. The ingredients corresponding to Example 15 are tabulated in Table 15 with the amount of each ingredient used in the process (i.e., the batch quantity) given in percent-by-weight (% w/w) and in milligrams. The amount of each ingredient provided in Table 15 corresponds to the formation of a single soft-chew tablet; however, as should be understood by those having ordinary skill in the art, the principles of Example 15 can be used to make more soft-chew tablets by proportionally increasing the amount of the ingredients as necessary to produce the desired quantity of soft-chew tablets.

TABLE 15

| Ingredient Name | Amount Per Unit (mg) | % w/w |
| --- | --- | --- |
| Carnauba wax | 120.000 | 3.810% |
| Citric acid anhydrous | 12.000 | 0.381% |
| Color agent (FD&C red) | 5.000 | 0.159% |
| Corn oil | 105.000 | 3.333% |
| Dried glucose syrup | 600.000 | 19.048% |
| Flavor agent (mixed berry) | 35.000 | 1.111% |
| Glycerin | 420.000 | 13.333% |
| Magnesium stearate | 10.500 | 0.333% |
| Maltitol solution | 240.000 | 7.619% |
| Mannitol | 607.000 | 19.270% |
| Milk powder | 553.000 | 17.556% |
| Partially pregelatinized starch | 290.700 | 9.229% |
| Sucralose | 1.800 | 0.057% |
| Sugar (extra fine caster) | 150.000 | 4.762% |
| TOTAL | 3150.000 | 100.000% |

Procedure—Example 15

Step 1: The batch quantity of dried glucose syrup along with, about 83% of the batch quantity of partially pregelatinized starch, 80% of the batch quantity of mannitol, and 78% of the batch quantity of milk powder were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of citric acid anhydrous and about 57% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of magnesium stearate was sifted using a No. 60 ASTM and collected in a polybag.

Step 7: The batch quantity of maltitol solution and the remaining batch quantity of flavor agent were added to the batch quantity of glycerin under continuous stirring.

Step 8: The batch quantity of sucralose was added to the mixture of Step 7 under continuous stirring.

Step 9: The batch quantity of color agent was added to the mixture of Step 8 under continuous stirring.

Step 10: The mixture of Step 9 was stirred until a uniform granulation dispersion was formed.

Step 11: The intragranular ingredient mixture of Step 2 was transferred to a rapid mixer granulator (with the impeller set to a slow speed and the chopper off) and mixed for approximately 10 minutes.

Step 12: The batch quantity of corn oil was slowly added to the mixture of Step 11 in a thin stream under continuous mixing (with the impeller set to a slow speed and the chopper on) with intermittent racking.

Step 13: The uniform granulation dispersion of Step 10 was slowly added to the mixture of Step 12 in a thin stream under continuous mixing (with the impeller set to a slow speed and the chopper on) with intermittent racking to form a wet mass.

Step 14: The wet mass of Step 13 and approximately 60% to 80% of the extragranular ingredient mixture of Step 4 were passed through a cone mill to form milled granules. The cone mill was fitted with a 4 mm screen, the knife was in the forward position, and the speed setting was slow.

Step 15: The milled granules of Step 14 along with the remaining extragranular ingredient mixture of Step 4 were co-sifted with a No. 8 ASTM to form granules. The granules were collected in a double-lined polybag.

Step 16: The granules of Step 15 were pre-lubricated using the carnauba wax of Step 5 for approximately 2-minutes.

Step 17: The granules of Step 16 were lubricated using the magnesium stearate of Step 6 for approximately 2-minutes.

Step 18: The granules from Step 17 were compressed using a rotary tablet press equipped with a square-shaped (approx. 18.5 mm by 18.5 mm) punch to form a compressed tablet.

Step 19: The tablets from Step 18 were coated using the batch quantity of sugar.

Example 16: A process for making soft-chew tablets in accordance with certain aspects of the present invention is provided in Example 16 below. The ingredients corresponding to Example 16 are tabulated in Table 16 with the amount of each ingredient used in the process (i.e., the batch quantity) given in percent-by-weight (% w/w) and in milligrams. The amount of each ingredient provided in Table 16 corresponds to the formation of a single soft-chew tablet; however, as should be understood by those having ordinary skill in the art, the principles of Example 16 can be used to make more soft-chew tablets by proportionally increasing the amount of the ingredients as necessary to produce the desired quantity of soft-chew tablets.

TABLE 16

| Ingredient Name | Amount Per Unit (mg) | % w/w |
| --- | --- | --- |
| Citric acid anhydrous | 2.000 | 0.222% |
| Corn oil | 30.000 | 3.333% |
| Dried glucose syrup | 200.000 | 22.222% |
| Flavor agent (grape) | 9.000 | 1.000% |

TABLE 16-continued

| Ingredient Name | Amount Per Unit (mg) | % w/w |
|---|---|---|
| Glycerin | 90.000 | 10.000% |
| Magnesium stearate | 10.000 | 1.111% |
| Maltitol solution | 80.000 | 8.889% |
| Mannitol | 253.500 | 28.167% |
| Partially pregelatinized starch | 100.000 | 11.111% |
| Sorbitol (powder) | 100.000 | 11.111% |
| Sucralose | 0.500 | 0.056% |
| Sugar (extra fine caster) | 25.000 | 2.778% |
| TOTAL | 900.000 | 100.000% |

Procedure—Example 16

Step 1: The batch quantities of dried glucose syrup and sorbitol (powder) along with, about 75% of the batch quantity of partially pregelatinized starch and 61% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and partially pregelatinized starch, along with about 67% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of magnesium stearate was sifted using a No. 60 ASTM and collected in a polybag.

Step 6: The batch quantity of maltitol solution and the remaining batch quantity of flavor agent were added to the batch quantity of glycerin under continuous stirring.

Step 7: The batch quantity of citric acid anhydrous was added to the mixture of Step 6 under continuous stirring.

Step 8: The batch quantity of sucralose was added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of corn oil was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 60% to 80% of the extragranular ingredient mixture of Step 4 were passed through a cone mill to form milled granules. The cone mill was fitted with a 4 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were lubricated using the magnesium stearate of Step 5 for approximately 2-minutes.

Step 16: The granules from Step 15 were compressed using a rotary tablet press equipped with a round-shaped (diameter of approx. 12 mm) PTFE punch to form a compressed tablet.

Step 17: The tablets from Step 16 were coated using the batch quantity of sugar.

Example 17: A process for making soft-chew tablets in accordance with certain aspects of the present invention is provided in Example 17 below. The ingredients corresponding to Example 17 are tabulated in Table 17 with the amount of each ingredient used in the process (i.e., the batch quantity) given in percent-by-weight (% w/w) and in milligrams. The amount of each ingredient provided in Table 17 corresponds to the formation of a single soft-chew tablet; however, as should be understood by those having ordinary skill in the art, the principles of Example 17 can be used to make more soft-chew tablets by proportionally increasing the amount of the ingredients as necessary to produce the desired quantity of soft-chew tablets.

TABLE 17

| Ingredient Name | Amount Per Unit (mg) | % w/w |
|---|---|---|
| Corn oil | 65.000 | 3.714% |
| Dried glucose syrup | 350.000 | 20.000% |
| Flavor agent (cool eucalyptus) | 6.000 | 0.343% |
| Flavor agent (cool mint) | 3.000 | 0.171% |
| Glycerin | 160.000 | 9.143% |
| Magnesium stearate | 17.500 | 1.000% |
| Maltitol solution | 150.000 | 8.571% |
| Mannitol | 413.800 | 23.646% |
| Partially pregelatinized starch | 184.000 | 10.514% |
| Sorbitol (powder) | 240.000 | 13.714% |
| Sucralose | 0.700 | 0.040% |
| Sugar (extra fine caster) | 40.000 | 2.286% |
| Xylitol | 120.000 | 6.857% |
| TOTAL | 1750.000 | 100.000% |

Procedure—Example 17

Step 1: The batch quantities of dried glucose syrup and sorbitol (powder) along with, about 71% of the batch quantity of partially pregelatinized starch and 69% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and partially pregelatinized starch, along with the batch quantity of flavor agent (cool mint) and the batch quantity of xylitol were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of magnesium stearate was sifted using a No. 60 ASTM and collected in a polybag.

Step 6: The batch quantities of maltitol solution and flavor agent (cool *eucalyptus*) were added to the batch quantity of glycerin under continuous stirring.

Step 7: The batch quantity of sucralose was added to the mixture of Step 6 under continuous stirring.

Step 8: The mixture of Step 7 was stirred until a uniform granulation dispersion was formed.

Step 9: The intragranular ingredient mixture of Step 2 was transferred to a rapid mixer granulator (with the impeller set to a slow speed and the chopper off) and mixed for approximately 10 minutes.

Step 10: The batch quantity of corn oil was slowly added to the mixture of Step 9 in a thin stream under continuous mixing (with the impeller set to a slow speed and the chopper on) with intermittent racking.

Step 11: The uniform granulation dispersion of Step 8 was slowly added to the mixture of Step 10 in a thin stream under continuous mixing (with the impeller set to a slow speed and the chopper on) with intermittent racking to form a wet mass.

Step 12: The wet mass of Step 11 and approximately 60% to 80% of the extragranular ingredient mixture of Step 4 were passed through a cone mill to form milled granules. The cone mill was fitted with a 4 mm screen, the knife was in the forward position, and the speed setting was slow.

Step 13: The milled granules of Step 12 along with the remaining extragranular ingredient mixture of Step 4 were co-sifted with a No. 8 ASTM to form granules. The granules were collected in a double-lined polybag.

Step 14: The granules of Step 13 were lubricated using the magnesium stearate of Step 5 for approximately 2-minutes.

Step 15: The granules from Step 14 were compressed using a rotary tablet press equipped with a round-shaped (diameter of approx. 16 mm) PTFE punch to form a compressed tablet.

Step 16: The tablets from Step 15 were coated using the batch quantity of sugar.

Example 18: A process for making soft-chew tablets in accordance with certain aspects of the present invention is provided in Example 18 below. The ingredients corresponding to Example 18 are tabulated in Table 18 with the amount of each ingredient used in the process (i.e., the batch quantity) given in percent-by-weight (% w/w) and in milligrams. In Example 18, the active ingredient is cyanocobalamin. Each soft-chew tablet formed by the process of Example 18 has an active strength of cyanocobalamin of about 2.5 mg. The amount of each ingredient provided in Table 18 corresponds to the formation of a single soft-chew tablet; however, as should be understood by those having ordinary skill in the art, the principles of Example 18 can be used to necessary to produce the desired quantity of soft-chew tablets.

TABLE 18

| Ingredient Name | Amount Per Unit (mg) | % w/w |
|---|---|---|
| Carnauba wax | 50.000 | 4.545% |
| Citric acid anhydrous | 5.400 | 0.491% |
| Color agent (FD&C red) | 1.350 | 0.123% |
| Croscarmellose sodium | 25.000 | 2.273% |
| Crospovidone | 25.000 | 2.273% |
| Cyanocobalamin | 2.500 | 0.227% |
| Dried glucose syrup | 155.000 | 14.091% |
| Flavor agent (mixed berry) | 12.000 | 1.091% |
| Glycerin | 120.000 | 10.909% |
| Maltitol solution | 100.000 | 9.091% |
| Mannitol | 277.500 | 25.227% |
| Milk powder | 80.000 | 7.273% |
| Partially pregelatinized starch | 65.600 | 5.964% |
| Simethicone | 100.000 | 9.091% |
| Sorbitol (powder) | 50.000 | 4.545% |
| Sucralose | 0.650 | 0.059% |
| Sugar (fine) | 30.000 | 2.727% |
| TOTAL | 1100.000 | 100.000% |

Procedure—Example 18

Step 1: The batch quantity of cyanocobalamin and approximately 9% of the batch quantity of mannitol were co-sifted with a No. 30 ASTM and collected in a polybag.

Step 2: The material of Step 1 and approximately 18% of the batch quantity of mannitol were co-sifted with a No. 30 ASTM and collected in a polybag.

Step 3: The material of Step 2 and approximately 27% of the batch quantity of mannitol were co-sifted with a No. 30 ASTM and collected in a polybag.

Step 4: The material of Step 3 and approximately 36% of the batch quantity of mannitol were co-sifted with a No. 30 ASTM and collected in a polybag.

Step 5: The material of Step 4 was sifted a second time with a No. 30 ASTM and collected in a polybag.

Step 6: The material of Step 5 along with the batch quantities of croscarmellose sodium, dried glucose syrup, sorbitol (powder); along with, 77% of the batch quantity of partially pregelatinized starch, and 63% of the batch quantity of milk powder were co-sifted with a No. 30 ASTM and collected in a polybag.

Step 7: The sifted ingredients of Step 6 were sifted a second time with a No. 30 ASTM to form an intragranular ingredient mixture, which was collected in a polybag.

Step 8: The remaining batch quantities of mannitol, milk powder, and partially pregelatinized starch, along with the batch quantity of crospovidone, about 70% of the batch quantity of citric acid anhydrous, and about 54% of the batch quantity of flavor agent were co-sifted with a No. 30 ASTM.

Step 9: The sifted ingredients of Step 8 were sifted a second time with a No. 30 ASTM to form an extragranular ingredient mixture, which was collected in a polybag.

Step 10: The batch quantity of carnauba wax was sifted using a No. 60 ASTM and collected in a polybag.

Step 11: The batch quantity of maltitol solution was added to the batch quantity of glycerin under continuous stirring.

Step 12: The batch quantity of color agent was added to the mixture of Step 11 under continuous stirring.

Step 13: The batch quantity of sucralose along with the remaining batch quantities of citric acid anhydrous and flavor agent were added to the mixture of Step 12 under continuous stirring.

Step 14: The mixture of Step 13 was stirred until a uniform granulation dispersion was formed.

Step 15: The intragranular ingredient mixture of Step 7 was transferred to a rapid mixer granulator (with the impeller set to a slow speed and the chopper off) and mixed for approximately 10 minutes.

Step 16: The batch quantity of simethicone was slowly added to the mixture of Step 15 in a thin stream under continuous mixing (with the impeller set to a slow speed and the chopper on) with intermittent racking.

Step 17: The uniform granulation dispersion of Step 14 was slowly added to the mixture of Step 16 in a thin stream under continuous mixing (with the impeller set to a slow speed and the chopper on) with intermittent racking to form a wet mass.

Step 18: The wet mass of Step 17 and approximately 75% of the extragranular ingredient mixture of Step 9 were passed through a cone mill to form milled granules. The cone mill was fitted with a 3 mm screen, the knife was in the forward position, and the speed setting was slow.

Step 19: The milled granules of Step 18 along with the remaining extragranular ingredient mixture of Step 9 were co-sifted with a No. 8 ASTM to form granules. The granules were collected in a double-lined polybag.

Step 20: The granules of Step 19 were sifted a second time with a No. 8 ASTM and collected in a double-lined polybag.

Step 21: The granules of Step 20 were lubricated using the carnauba wax of Step 10 for approximately 2-minutes.

Step 22: The granules from Step 21 were compressed using a rotary tablet press equipped with a round-shaped (diameter of approx. 12 mm) PTFE punch to form a compressed tablet.

Step 23: The tablets from Step 22 were coated using the batch quantity of sugar.

Example 19: A process for making soft-chew tablets in accordance with certain aspects of the present invention is provided in Example 19 below. The ingredients corresponding to Example 19 are tabulated in Table 19 with the amount of each ingredient used in the process (i.e., the batch quantity) given in percent-by-weight (% w/w) and in milligrams. In Example 19, the active ingredient is biotin. Each soft-chew tablet formed by the process of Example 19 has an active strength of biotin of about 10 mg. The amount of each ingredient provided in Table 19 corresponds to the formation of a single soft-chew tablet; however, as should be understood by those having ordinary skill in the art, the principles of Example 19 can be used to make more soft-chew tablets by proportionally increasing the amount of the ingredients as necessary to produce the desired quantity of soft-chew tablets.

TABLE 19

| Ingredient Name | Amount Per Unit (mg) | % w/w |
|---|---|---|
| Biotin | 10.000 | 1.000% |
| Carnauba wax | 50.000 | 5.000% |
| Citric acid anhydrous | 5.400 | 0.540% |
| Color agent (FD&C red) | 1.350 | 0.135% |
| Croscarmellose sodium | 27.000 | 2.700% |
| Crospovidone | 27.000 | 2.700% |
| Dried glucose syrup | 160.000 | 16.000% |
| Flavor agent (mixed berry) | 12.000 | 1.200% |
| Glycerin | 100.000 | 10.000% |
| Maltitol solution | 75.000 | 7.500% |
| Mannitol | 126.600 | 12.660% |
| Milk powder | 140.000 | 14.000% |
| Partially pregelatinized starch | 81.000 | 8.100% |
| Simethicone | 100.000 | 10.000% |
| Sorbitol (powder) | 54.000 | 5.400% |
| Sucralose | 0.650 | 0.065% |
| Sugar (fine) | 30.000 | 3.000% |
| TOTAL | 1000.000 | 100.000% |

Procedure—Example 19

Step 1: The batch quantities of croscarmellose sodium, dried glucose syrup, and sorbitol (powder) along with, about 80% of the batch quantity of partially pregelatinized starch, 79% of the batch quantity of milk powder, and 76% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone, 70% of the batch quantity of citric acid anhydrous and 54% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of biotin was added to the mixture of Step 6 under continuous stirring.

Step 8: The batch quantity of color agent was added to the mixture of Step 7 under continuous stirring.

Step 9: The batch quantity of sucralose along with the remaining batch quantities of citric acid anhydrous and flavor agent were added to the mixture of Step 8 under continuous stirring.

Step 10: The mixture of Step 9 was stirred until a uniform granulation dispersion was formed.

Step 11: The intragranular ingredient mixture of Step 2 was transferred to a rapid mixer granulator (with the impeller set to a slow speed and the chopper off) and mixed for approximately 10 minutes.

Step 12: The batch quantity of simethicone was slowly added to the mixture of Step 11 in a thin stream under continuous mixing (with the impeller set to a slow speed and the chopper on) with intermittent racking.

Step 13: The uniform granulation dispersion of Step 10 was slowly added to the mixture of Step 12 in a thin stream under continuous mixing (with the impeller set to a slow speed and the chopper on) with intermittent racking to form a wet mass.

Step 14: The wet mass of Step 13 and approximately 75% of the extragranular ingredient mixture of Step 4 were passed through a cone mill to form milled granules. The cone mill was fitted with a 3 mm screen, the knife was in the forward position, and the speed setting was slow.

Step 15: The milled granules of Step 14 along with the remaining extragranular ingredient mixture of Step 4 were co-sifted with a No. 8 ASTM to form granules. The granules were collected in a double-lined polybag.

Step 16: The granules of Step 15 were sifted a second time with a No. 8 ASTM and collected in a double-lined polybag.

Step 17: The granules of Step 16 were lubricated using the carnauba wax of Step 5 for approximately 2-minutes.

Step 18: The granules from Step 17 were compressed using a rotary tablet press equipped with a round-shaped (diameter of approx. 12 mm) PTFE punch to form a compressed tablet.

Step 19: The tablets from Step 18 were coated using the batch quantity of sugar.

Example 20: A process for making soft-chew tablets in accordance with certain aspects of the present invention is provided in Example 20 below. The ingredients corresponding to Example 20 are tabulated in Table 20 with the amount of each ingredient used in the process (i.e., the batch quantity) given in percent-by-weight (% w/w) and in milligrams. In Example 20, the active ingredients are calcium carbonate and simethicone. Each soft-chew tablet formed by the process of Example 20 has an active strength of calcium carbonate of approximately 1334 mg and an active strength of simethicone of about 264 mg. The amount of each ingredient provided in Table 20 corresponds to the formation of a single soft-chew tablet; however, as should be understood by those having ordinary skill in the art, the principles of Example 20 can be used to make more soft-chew tablets by proportionally increasing the amount of the ingredients as necessary to produce the desired quantity of soft-chew tablets.

TABLE 20

| Ingredient Name | Amount Per Unit (mg) | % w/w |
|---|---|---|
| Calcium carbonate | 1333.950 | 41.299% |
| Carnauba wax | 100.000 | 3.096% |
| Color agent (FD&C red) | 4.000 | 0.124% |
| Croscarmellose sodium | 60.000 | 1.858% |
| Crospovidone | 20.000 | 0.619% |
| Dried glucose syrup | 305.200 | 9.449% |
| Flavor agent (mixed berry) | 48.000 | 1.486% |
| Glycerin | 300.000 | 9.288% |
| Maltitol solution | 170.000 | 5.263% |
| Milk powder | 280.000 | 8.669% |
| Partially pregelatinized starch | 150.000 | 4.644% |
| Polyvinylpyrrolidone | 30.000 | 0.929% |
| Simethicone | 263.850 | 8.169% |
| Sorbitol (powder) | 110.000 | 3.406% |
| Sucralose | 5.000 | 0.155% |
| Sugar (caster sugar) | 50.000 | 1.548% |
| TOTAL | 3230.000 | 100.000% |

Procedure—Example 20

Step 1: The batch quantities of calcium carbonate and dried glucose syrup along with, about 71% of the batch quantity of milk powder, 67% of the batch quantity of croscarmellose sodium, 67% of the batch quantity of partially pregelatinized starch, and 45% of the batch quantity of sorbitol (powder) were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of croscarmellose sodium, milk powder, partially pregelatinized starch, and sorbitol (powder) along with the batch quantity of crospovidone and about 63% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The remaining batch quantity of flavor agent was added to the mixture of Step 6 under continuous stirring.

Step 8: The batch quantities of color agent, polyvinylpyrrolidone, and sucralose were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 20 mm) PTFE punch to form a compressed tablet.

Step 18: The tablets from Step 17 were coated using the batch quantity of sugar.

Example 21: A process for making soft-chew tablets in accordance with certain aspects of the present invention is provided in Example 21 below. The ingredients corresponding to Example 21 are tabulated in Table 21 with the amount of each ingredient used in the process (i.e., the batch quantity) given in percent-by-weight (% w/w) and in milligrams. In Example 21, the active ingredients are calcium carbonate and simethicone. Each soft-chew tablet formed by the process of Example 21 has an active strength of calcium carbonate of approximately 1372 mg and an active strength of simethicone of about 128 mg. The amount of each ingredient provided in Table 21 corresponds to the formation of a single soft-chew tablet; however, as should be understood by those having ordinary skill in the art, the principles of Example 21 can be used to make more soft-chew tablets by proportionally increasing the amount of the ingredients as necessary to produce the desired quantity of soft-chew tablets.

TABLE 21

| Ingredient Name | Amount Per Unit (mg) | % w/w |
|---|---|---|
| Calcium carbonate | 1372.400 | 34.224% |
| Carnauba wax | 90.000 | 2.244% |
| Color agent (FD&C red) | 2.000 | 0.050% |
| Corn oil | 105.000 | 2.618% |
| Dried glucose syrup | 290.000 | 7.232% |
| Flavor agent (mixed berry) | 80.000 | 1.995% |
| Glycerin | 400.000 | 9.975% |
| Hydroxypropyl beta-cyclodextrin | 130.000 | 3.242% |
| Magnesium hydroxide | 296.000 | 7.382% |
| Maltitol solution | 270.000 | 6.733% |
| Mannitol | 300.790 | 7.501% |
| Milk powder | 345.000 | 8.603% |
| Partially pregelatinized starch | 125.000 | 3.117% |
| Simethicone | 127.810 | 3.187% |
| Sucralose | 6.000 | 0.150% |
| Sugar (caster sugar) | 70.000 | 1.746% |
| TOTAL | 4010.000 | 100.000% |

Procedure—Example 21

Step 1: The batch quantities of calcium carbonate, dried glucose syrup, magnesium hydroxide, and simethicone along with, about 77% of the batch quantity of hydroxypropyl beta-cyclodextrin, 67% of the batch quantity of mannitol, 66% of the batch quantity of milk powder, and 20% of the batch quantity of partially pregelatinized starch were co-sifted with a No. 40 ASTM.

Step 2: The sifted ingredients of Step 1 were sifted a second time with a No. 40 ASTM to form an intragranular ingredient mixture, which was collected in a polybag.

Step 3: The remaining batch quantities of mannitol, milk powder, and partially pregelatinized starch were co-sifted with a No. 40 ASTM.

Step 4: The sifted ingredients of Step 3 were sifted a second time with a No. 40 ASTM to form an extragranular ingredient mixture, which was collected in a polybag.

Step 5: The batch quantity of carnauba wax was sifted using a No. 60 ASTM and collected in a polybag.

Step 6: The batch quantity of color agent was added to the batch quantity of glycerin under continuous stirring.

Step 7: The batch quantity of sucralose and the remaining batch quantity of hydroxypropyl beta-cyclodextrin were added to the mixture of Step 6 under continuous stirring.

Step 8: The batch quantities of flavor agent and maltitol solution were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of corn oil was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 4 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 20 mm) PTFE punch to form a compressed tablet.

Step 18: The tablets from Step 17 were coated using the batch quantity of sugar.

Example 22: A process for making soft-chew tablets in accordance with certain aspects of the present invention is provided in Example 22 below. The ingredients corresponding to Example 22 are tabulated in Table 22 with the amount of each ingredient used in the process (i.e., the batch quantity) given in percent-by-weight (% w/w) and in milligrams. In Example 22, the active ingredient is simethicone. Each soft-chew tablet formed by the process of Example 22 has an active strength of simethicone of about 264 mg. The amount of each ingredient provided in Table 22 corresponds to the formation of a single soft-chew tablet; however, as should be understood by those having ordinary skill in the art, the principles of Example 22 can be used to make more soft-chew tablets by proportionally increasing the amount of the ingredients as necessary to produce the desired quantity of soft-chew tablets.

TABLE 22

| Ingredient Name | Amount Per Unit (mg) | % w/w |
| --- | --- | --- |
| Carnauba wax | 15.600 | 0.800% |
| Citric acid anhydrous | 10.080 | 0.517% |
| Color agent (FD&C red) | 2.540 | 0.130% |
| Croscarmellose sodium | 53.000 | 2.718% |
| Crospovidone | 53.000 | 2.718% |
| Dried glucose syrup | 321.550 | 16.490% |
| Flavor agent (mixed berry) | 22.790 | 1.169% |
| Glycerin | 131.520 | 6.745% |
| Maltitol solution | 141.120 | 7.237% |
| Mannitol | 344.730 | 17.678% |
| Milk powder | 273.000 | 14.000% |
| Partially pregelatinized starch | 158.000 | 8.103% |
| Simethicone | 263.850 | 13.531% |
| Sorbitol powder | 105.000 | 5.385% |
| Sucralose | 1.220 | 0.063% |
| Sugar (caster sugar) | 53.000 | 2.718% |
| TOTAL | 1950.000 | 100.000% |

Procedure—Example 22

Step 1: The batch quantities of croscarmellose sodium, dried glucose syrup, and sorbitol (powder) along with, about 80% of the batch quantity of partially pregelatinized starch, 77% of the batch quantity of milk powder, and 82% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone and 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 40 ASTM and collected in a polybag.

Step 6: The batch quantity of maltitol solution was added to the batch quantity of glycerin under continuous stirring.

Step 7: The batch quantity of sucralose was added to the mixture of Step 6 under continuous stirring.

Step 8: The batch quantities of sucralose and citric acid anhydrous along with the remaining batch quantity of flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 5 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a square-shaped (approx. 15.3 mm by 15.3 mm) PTFE punch, having the number "7" embossed on one side, to form a compressed tablet.

Step 18: The tablets from Step 17 were coated using the batch quantity of sugar.

Example 23: A process for making soft-chew tablets in accordance with certain aspects of the present invention is provided in Example 23 below. The ingredients corresponding to Example 23 are tabulated in Table 23 with the amount of each ingredient used in the process (i.e., the batch quantity) given in percent-by-weight (% w/w) and in milligrams. In Example 23, the active ingredient is omega-3 oils. Each soft-chew tablet formed by the process of Example 23 has an active strength of omega-3 oils of about 500 mg. The amount of each ingredient provided in Table 23 corresponds to the formation of a single soft-chew tablet; however, as should be understood by those having ordinary skill in the art, the principles of Example 23 can be used to make more soft-chew tablets by proportionally increasing the amount of the ingredients as necessary to produce the desired quantity of soft-chew tablets.

TABLE 23

| Ingredient Name | Amount Per Unit (mg) | % w/w |
|---|---|---|
| Availom 50 High DHA* | 1000.000 | 32.258% |
| Carnauba wax | 25.000 | 0.806% |
| Citric acid anhydrous | 15.000 | 0.484% |
| Color agent (orange iron oxide) | 4.000 | 0.129% |
| Croscarmellose sodium | 50.000 | 1.613% |
| Crospovidone | 50.000 | 1.613% |
| Dried glucose syrup | 250.000 | 8.065% |
| Flavor agent (orange) | 45.000 | 1.452% |
| Glycerin | 300.000 | 9.677% |
| Maltitol solution | 300.000 | 9.677% |
| Maltodextrin | 100.000 | 3.226% |
| Mannitol | 228.500 | 7.371% |
| Milk powder | 230.000 | 7.419% |
| Partially pregelatinized starch | 100.000 | 3.226% |
| Potassium sorbate | 50.000 | 1.613% |
| Sodium benzoate | 20.000 | 0.645% |
| Sorbitol (powder) | 100.000 | 3.226% |
| Sugar (fine) | 80.000 | 2.581% |
| Thyme oil | 100.000 | 3.226% |
| Tocopherol | 2.500 | 0.081% |
| Xanthan gum | 50.000 | 1.613% |
| TOTAL | 3100.000 | 100.000% |

*1000 mg of Availom 50 High DHA contains 500 mg of Omega 3.

Procedure—Example 23

Step 1: The batch quantities of Availom 50 high DHA, croscarmellose sodium, dried glucose syrup, maltodextrin, potassium sorbate, sodium benzoate, sorbitol (powder), and xanthan gum along with, about 50% of the batch quantity of partially pregelatinized starch, 65% of the batch quantity of milk powder, and 65% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone and 56% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantities of citric acid anhydrous and tocopherol along with the remaining batch quantity of flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of thyme oil was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 4 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 20 mm) PTFE punch to form a compressed tablet.

Step 18: The tablets from Step 17 were coated using the batch quantity of sugar.

Example 24: A process for making soft-chew tablets in accordance with certain aspects of the present invention is provided in Example 24 below. The ingredients corresponding to Example 24 are tabulated in Table 24 with the amount of each ingredient used in the process (i.e., the batch quantity) given in percent-by-weight (% w/w) and in milligrams. In Example 24, the active ingredient is omega-3 oils. Each soft-chew tablet formed by the process of Example 24 has an active strength of omega-3 oils of about 500 mg. The amount of each ingredient provided in Table 24 corresponds to the formation of a single soft-chew tablet; however, as should be understood by those having ordinary skill in the art, the principles of Example 24 can be used to make more soft-chew tablets by proportionally increasing the amount of the ingredients as necessary to produce the desired quantity of soft-chew tablets.

TABLE 24

| Ingredient Name | Amount Per Unit (mg) | % w/w |
| --- | --- | --- |
| Albumin | 50.000 | 1.587% |
| Availom 50 High DHA* | 1000.000 | 31.746% |
| Carnauba wax | 25.000 | 0.794% |
| Citric acid anhydrous | 15.000 | 0.476% |
| Color agent (orange iron oxide) | 4.000 | 0.127% |
| Croscarmellose sodium | 50.000 | 1.587% |
| Crospovidone | 50.000 | 1.587% |
| Dried glucose syrup | 250.000 | 7.937% |
| Flavor agent (orange) | 45.000 | 1.429% |
| Glycerin | 300.000 | 9.524% |
| Maltitol solution | 300.000 | 9.524% |
| Maltodextrin | 100.000 | 3.175% |
| Mannitol | 218.500 | 6.937% |
| Milk powder | 230.000 | 7.302% |
| Partially pregelatinized starch | 50.000 | 1.587% |
| Sodium benzoate | 70.000 | 2.222% |
| Sodium caseinate | 50.000 | 1.587% |
| Sorbitol (powder) | 100.000 | 3.175% |
| Soy protein | 50.000 | 1.587% |
| Soya lecithin | 10.000 | 0.317% |
| Sugar (fine) | 80.000 | 2.540% |
| Thyme oil | 100.000 | 3.175% |
| Tocopherol | 2.500 | 0.079% |
| TOTAL | 3150.000 | 100.000% |

*1000 mg of Availom 50 High DHA contains 500 mg of Omega 3.

Procedure—Example 24

Step 1: The batch quantities of albumin, Availom 50 high DHA, croscarmellose sodium, dried glucose syrup, maltodextrin, sodium benzoate, sodium caseinate, sorbitol (powder), and soy protein along with, about 65% of the batch quantity of milk powder and 63% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and milk powder, along with the batch quantity of crospovidone, the batch quantity of partially pregelatinized starch, and about 56% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantities of soya lecithin and tocopherol were added to the mixture of Step 7 under continuous stirring.

Step 9: The batch quantity of citric acid anhydrous along with the remaining batch quantity of flavor agent were added to the mixture of Step 8 under continuous stirring.

Step 10: The mixture of Step 9 was stirred until a uniform granulation dispersion was formed.

Step 11: The intragranular ingredient mixture of Step 2 was transferred to a rapid mixer granulator (with the impeller set to a slow speed and the chopper off) and mixed for approximately 10 minutes.

Step 12: The batch quantity of thyme oil was slowly added to the mixture of Step 11 in a thin stream under continuous mixing (with the impeller set to a slow speed and the chopper on) with intermittent racking.

Step 13: The uniform granulation dispersion of Step 10 was slowly added to the mixture of Step 12 in a thin stream under continuous mixing (with the impeller set to a slow speed and the chopper on) with intermittent racking to form a wet mass.

Step 14: The wet mass of Step 13 and approximately 75% of the extragranular ingredient mixture of Step 4 were passed through a cone mill to form milled granules. The cone mill was fitted with a 4 mm screen, the knife was in the forward position, and the speed setting was slow.

Step 15: The milled granules of Step 14 along with the remaining extragranular ingredient mixture of Step 4 were co-sifted with a No. 8 ASTM to form granules. The granules were collected in a double-lined polybag.

Step 16: The granules of Step 15 were sifted a second time with a No. 8 ASTM and collected in a double-lined polybag.

Step 17: The granules of Step 16 were lubricated using the carnauba wax of Step 5 for approximately 2-minutes.

Step 18: The granules from Step 17 were compressed using a rotary tablet press equipped with a round-shaped (diameter of approx. 20 mm) PTFE punch to form a compressed tablet.

Step 19: The tablets from Step 18 were coated using the batch quantity of sugar.

Example 25: A process for making soft-chew tablets in accordance with certain aspects of the present invention is provided in Example 25 below. The ingredients corresponding to Example 25 are tabulated in Table 25 with the amount of each ingredient used in the process (i.e., the batch quantity) given in percent-by-weight (% w/w) and in milligrams. In Example 25, the active ingredient is omega-3 oils. Each soft-chew tablet formed by the process of Example 25 has an active strength of omega-3 oils of about 500 mg. The amount of each ingredient provided in Table 25 corresponds to the formation of a single soft-chew tablet; however, as should be understood by those having ordinary skill in the art, the principles of Example 25 can be used to make more soft-chew tablets by proportionally increasing the amount of the ingredients as necessary to produce the desired quantity of soft-chew tablets.

TABLE 25

| Ingredient Name | Amount Per Unit (mg) | % w/w |
| --- | --- | --- |
| Albumin | 100.000 | 3.125% |
| Availom 50 High DHA* | 1000.000 | 31.250% |
| Carnauba wax | 25.000 | 0.781% |
| Citric acid anhydrous | 15.000 | 0.469% |
| Color agent (orange iron oxide) | 4.000 | 0.125% |
| Croscarmellose sodium | 50.000 | 1.563% |

TABLE 25-continued

| Ingredient Name | Amount Per Unit (mg) | % w/w |
|---|---|---|
| Crospovidone | 50.000 | 1.563% |
| Dried glucose syrup | 250.000 | 7.813% |
| Flavor agent (orange) | 45.000 | 1.406% |
| Glycerin | 300.000 | 9.375% |
| Maltitol solution | 300.000 | 9.375% |
| Maltodextrin | 50.000 | 1.563% |
| Mannitol | 178.500 | 5.578% |
| Milk powder | 230.000 | 7.188% |
| Partially pregelatinized starch | 50.000 | 1.563% |
| Potassium sorbate | 70.000 | 2.188% |
| Sodium caseinate | 50.000 | 1.563% |
| Sorbitol (powder) | 100.000 | 3.125% |
| Sugar (fine) | 80.000 | 2.500% |
| Thyme oil | 100.000 | 3.125% |
| Tocopherol | 2.500 | 0.078% |
| Whey protein | 150.000 | 4.688% |
| TOTAL | 3200.000 | 100.000% |

*1000 mg of Availom 50 High DHA contains 500 mg of Omega 3.

Procedure—Example 25

Step 1: The batch quantities of albumin, Availom 50 high DHA, croscarmellose sodium, dried glucose syrup, maltodextrin, potassium sorbate, sodium caseinate, sorbitol (powder), and whey protein along with, about 65% of the batch quantity of milk powder and 55% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and milk powder, along with the batch quantity of crospovidone, the batch quantity of partially pregelatinized starch, and about 56% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of tocopherol was added to the mixture of Step 7 under continuous stirring.

Step 9: The batch quantity of citric acid anhydrous along with the remaining batch quantity of flavor agent were added to the mixture of Step 8 under continuous stirring.

Step 10: The mixture of Step 9 was stirred until a uniform granulation dispersion was formed.

Step 11: The intragranular ingredient mixture of Step 2 was transferred to a rapid mixer granulator (with the impeller set to a slow speed and the chopper off) and mixed for approximately 10 minutes.

Step 12: The batch quantity of thyme oil was slowly added to the mixture of Step 11 in a thin stream under continuous mixing (with the impeller set to a slow speed and the chopper on) with intermittent racking.

Step 13: The uniform granulation dispersion of Step 10 was slowly added to the mixture of Step 12 in a thin stream under continuous mixing (with the impeller set to a slow speed and the chopper on) with intermittent racking to form a wet mass.

Step 14: The wet mass of Step 13 and approximately 75% of the extragranular ingredient mixture of Step 4 were passed through a cone mill to form milled granules. The cone mill was fitted with a 4 mm screen, the knife was in the forward position, and the speed setting was slow.

Step 15: The milled granules of Step 14 along with the remaining extragranular ingredient mixture of Step 4 were co-sifted with a No. 8 ASTM to form granules. The granules were collected in a double-lined polybag.

Step 16: The granules of Step 15 were sifted a second time with a No. 8 ASTM and collected in a double-lined polybag.

Step 17: The granules of Step 16 were lubricated using the carnauba wax of Step 5 for approximately 2-minutes.

Step 18: The granules from Step 17 were compressed using a rotary tablet press equipped with a round-shaped (diameter of approx. 20 mm) PTFE punch to form a compressed tablet.

Step 19: The tablets from Step 18 were coated using the batch quantity of sugar.

Example 26: A process for making soft-chew tablets in accordance with certain aspects of the present invention is provided in Example 26 below. The ingredients corresponding to Example 26 are tabulated in Table 26 with the amount of each ingredient used in the process (i.e., the batch quantity) given in percent-by-weight (% w/w) and in milligrams. In Example 26, the active ingredient is omega-3 oils. Each soft-chew tablet formed by the process of Example 26 has an active strength of omega-3 oils of about 255 mg. The amount of each ingredient provided in Table 26 corresponds to the formation of a single soft-chew tablet; however, as should be understood by those having ordinary skill in the art, the principles of Example 26 can be used to make more soft-chew tablets by proportionally increasing the amount of the ingredients as necessary to produce the desired quantity of soft-chew tablets.

TABLE 26

| Ingredient Name | Amount Per Unit (mg) | % w/w |
|---|---|---|
| Carnauba wax | 24.000 | 1.000% |
| Citric acid anhydrous | 9.200 | 0.383% |
| Color agent (FD&C red) | 2.350 | 0.098% |
| Croscarmellose sodium | 45.000 | 1.875% |
| Crospovidone | 45.000 | 1.875% |
| Dried glucose syrup | 250.000 | 10.417% |
| Flavor agent (tangerine) | 10.800 | 0.450% |
| Glycerin | 280.000 | 11.667% |
| Maltitol solution | 280.000 | 11.667% |
| Mannitol | 243.650 | 10.152% |
| Milk powder | 205.000 | 8.542% |
| Omega 3 Powder* | 600.000 | 25.000% |
| Partially pregelatinized starch | 110.000 | 4.583% |
| Simethicone | 150.000 | 6.250% |
| Sorbitol (powder) | 95.000 | 3.958% |
| Sugar (fine) | 50.000 | 2.083% |
| TOTAL | 2400.000 | 100.000% |

*600 mg of Omega 3 powder contains 255.0 mg of Omega 3.

Procedure—Example 26

Step 1: The batch quantities of croscarmellose sodium, dried glucose syrup, omega 3 powder, and sorbitol (powder) along with, about 78% of the batch quantity of mannitol, 73% of the batch quantity of milk powder, 73% of the batch quantity of partially pregelatinized starch, and 50% of the batch quantity of flavor agent were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of citric acid anhydrous was added to the mixture of Step 7 under continuous stirring.

Step 9: The remaining batch quantity of flavor agent was added to the mixture of Step 8 under continuous stirring.

Step 10: The mixture of Step 9 was stirred until a uniform granulation dispersion was formed.

Step 11: The intragranular ingredient mixture of Step 2 was transferred to a rapid mixer granulator (with the impeller set to a slow speed and the chopper off) and mixed for approximately 10 minutes.

Step 12: The batch quantity of simethicone was slowly added to the mixture of Step 11 in a thin stream under continuous mixing (with the impeller set to a slow speed and the chopper on) with intermittent racking.

Step 13: The uniform granulation dispersion of Step 10 was slowly added to the mixture of Step 12 in a thin stream under continuous mixing (with the impeller set to a slow speed and the chopper on) with intermittent racking to form a wet mass.

Step 14: The wet mass of Step 13 and approximately 75% of the extragranular ingredient mixture of Step 4 were passed through a cone mill to form milled granules. The cone mill was fitted with a 4 mm screen, the knife was in the forward position, and the speed setting was slow.

Step 15: The milled granules of Step 14 along with the remaining extragranular ingredient mixture of Step 4 were co-sifted with a No. 8 ASTM to form granules. The granules were collected in a double-lined polybag.

Step 16: The granules of Step 15 were sifted a second time with a No. 8 ASTM and collected in a double-lined polybag.

Step 17: The granules of Step 16 were lubricated using the carnauba wax of Step 5 for approximately 2-minutes.

Step 18: The granules from Step 17 were compressed using a rotary tablet press equipped with a round-shaped (diameter of approx. 20 mm) PTFE punch to form a compressed tablet.

Step 19: The tablets from Step 18 were coated using the batch quantity of sugar.

Example 27: A process for making soft-chew tablets in accordance with certain aspects of the present invention is provided in Example 27 below. The ingredients corresponding to Example 27 are tabulated in Table 27 with the amount of each ingredient used in the process (i.e., the batch quantity) given in percent-by-weight (% w/w) and in milligrams. In Example 27, the active ingredient is omega-3 oils. Each soft-chew tablet formed by the process of Example 27 has an active strength of omega-3 oils of about 510 mg. The amount of each ingredient provided in Table 27 corresponds to the formation of a single soft-chew tablet; however, as should be understood by those having ordinary skill in the art, the principles of Example 27 can be used to make more soft-chew tablets by proportionally increasing the amount of the ingredients as necessary to produce the desired quantity of soft-chew tablets.

TABLE 27

| Ingredient Name | Amount Per Unit (mg) | % w/w |
|---|---|---|
| Carnauba wax | 24.000 | 0.800% |
| Citric acid anhydrous | 9.200 | 0.307% |
| Color agent (FD&C red) | 2.350 | 0.078% |
| Croscarmellose sodium | 45.000 | 1.500% |
| Crospovidone | 45.000 | 1.500% |
| Dried glucose syrup | 250.000 | 8.333% |
| Flavor agent (tangerine) | 10.800 | 0.360% |
| Glycerin | 280.000 | 9.333% |
| Maltitol solution | 280.000 | 9.333% |
| Mannitol | 243.650 | 8.122% |
| Milk powder | 205.000 | 6.833% |
| Omega 3 Powder* | 1200.000 | 40.000% |
| Partially pregelatinized starch | 110.000 | 3.667% |
| Simethicone | 150.000 | 5.000% |
| Sorbitol (powder) | 95.000 | 3.167% |
| Sugar (fine) | 50.000 | 1.667% |
| TOTAL | 3000.000 | 100.000% |

*1200 mg of Omega 3 powder contains 510.0 mg of Omega 3.

Procedure—Example 27

Step 1: The batch quantities of croscarmellose sodium, dried glucose syrup, omega 3 powder, and sorbitol (powder) along with, about 78% of the batch quantity of mannitol, 73% of the batch quantity of milk powder, 73% of the batch quantity of partially pregelatinized starch, and 50% of the batch quantity of flavor agent were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of citric acid anhydrous was added to the mixture of Step 7 under continuous stirring.

Step 9: The remaining batch quantity of flavor agent was added to the mixture of Step 8 under continuous stirring.

Step 10: The mixture of Step 9 was stirred until a uniform granulation dispersion was formed.

Step 11: The intragranular ingredient mixture of Step 2 was transferred to a rapid mixer granulator (with the impeller set to a slow speed and the chopper off) and mixed for approximately 10 minutes.

Step 12: The batch quantity of simethicone was slowly added to the mixture of Step 11 in a thin stream under continuous mixing (with the impeller set to a slow speed and the chopper on) with intermittent racking.

Step 13: The uniform granulation dispersion of Step 10 was slowly added to the mixture of Step 12 in a thin stream under continuous mixing (with the impeller set to a slow speed and the chopper on) with intermittent racking to form a wet mass.

Step 14: The wet mass of Step 13 and approximately 75% of the extragranular ingredient mixture of Step 4 were passed through a cone mill to form milled granules. The cone mill was fitted with a 4 mm screen, the knife was in the forward position, and the speed setting was slow.

Step 15: The milled granules of Step 14 along with the remaining extragranular ingredient mixture of Step 4 were co-sifted with a No. 8 ASTM to form granules. The granules were collected in a double-lined polybag.

Step 16: The granules of Step 15 were sifted a second time with a No. 8 ASTM and collected in a double-lined polybag.

Step 17: The granules of Step 16 were lubricated using the carnauba wax of Step 5 for approximately 2-minutes.

Step 18: The granules from Step 17 were compressed using a rotary tablet press equipped with a round-shaped (diameter of approx. 20 mm) PTFE punch to form a compressed tablet.

Step 19: The tablets from Step 18 were coated using the batch quantity of sugar.

Example 28: A process for making soft-chew tablets in accordance with certain aspects of the present invention is provided in Example 28 below. The ingredients corresponding to Example 28 are tabulated in Table 28 with the amount of each ingredient used in the process (i.e., the batch quantity) given in percent-by-weight (% w/w) and in milligrams. In Example 28, the active ingredient is omega-3 oils. Each soft-chew tablet formed by the process of Example 28 has an active strength of omega-3 oils of about 637.5 mg. The amount of each ingredient provided in Table 28 corresponds to the formation of a single soft-chew tablet; however, as should be understood by those having ordinary skill in the art, the principles of Example 28 can be used to make more soft-chew tablets by proportionally increasing the amount of the ingredients as necessary to produce the desired quantity of soft-chew tablets.

TABLE 28

| Ingredient Name | Amount Per Unit (mg) | % w/w |
| --- | --- | --- |
| Carnauba wax | 24.000 | 0.727% |
| Citric acid anhydrous | 9.200 | 0.279% |
| Color agent (FD&C red) | 2.350 | 0.071% |
| Croscarmellose sodium | 45.000 | 1.364% |
| Crospovidone | 45.000 | 1.364% |
| Dried glucose syrup | 250.000 | 7.576% |
| Flavor agent (tangerine) | 10.800 | 0.327% |
| Glycerin | 280.000 | 8.485% |
| Maltitol solution | 280.000 | 8.485% |
| Mannitol | 243.650 | 7.383% |
| Milk powder | 205.000 | 6.212% |
| Omega 3 Powder* | 1500.000 | 45.455% |
| Partially pregelatinized starch | 110.000 | 3.333% |
| Simethicone | 150.000 | 4.545% |
| Sorbitol (powder) | 95.000 | 2.879% |
| Sugar (fine) | 50.000 | 1.515% |
| TOTAL | 3300.000 | 100.000% |

*1500 mg of Omega 3 powder contains 637.5 mg of Omega 3.

Procedure—Example 28

Step 1: The batch quantities of croscarmellose sodium, dried glucose syrup, omega 3 powder, and sorbitol (powder) along with, about 78% of the batch quantity of mannitol, 73% of the batch quantity of milk powder, 73% of the batch quantity of partially pregelatinized starch, and 50% of the batch quantity of flavor agent were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of citric acid anhydrous was added to the mixture of Step 7 under continuous stirring.

Step 9: The remaining batch quantity of flavor agent was added to the mixture of Step 8 under continuous stirring.

Step 10: The mixture of Step 9 was stirred until a uniform granulation dispersion was formed.

Step 11: The intragranular ingredient mixture of Step 2 was transferred to a rapid mixer granulator (with the impeller set to a slow speed and the chopper off) and mixed for approximately 10 minutes.

Step 12: The batch quantity of simethicone was slowly added to the mixture of Step 11 in a thin stream under continuous mixing (with the impeller set to a slow speed and the chopper on) with intermittent racking.

Step 13: The uniform granulation dispersion of Step 10 was slowly added to the mixture of Step 12 in a thin stream under continuous mixing (with the impeller set to a slow speed and the chopper on) with intermittent racking to form a wet mass.

Step 14: The wet mass of Step 13 and approximately 75% of the extragranular ingredient mixture of Step 4 were passed through a cone mill to form milled granules. The cone mill was fitted with a 4 mm screen, the knife was in the forward position, and the speed setting was slow.

Step 15: The milled granules of Step 14 along with the remaining extragranular ingredient mixture of Step 4 were co-sifted with a No. 8 ASTM to form granules. The granules were collected in a double-lined polybag.

Step 16: The granules of Step 15 were sifted a second time with a No. 8 ASTM and collected in a double-lined polybag.

Step 17: The granules of Step 16 were lubricated using the carnauba wax of Step 5 for approximately 2-minutes.

Step 18: The granules from Step 17 were compressed using a rotary tablet press equipped with a round-shaped (diameter of approx. 20 mm) PTFE punch to form a compressed tablet.

Step 19: The tablets from Step 18 were coated using the batch quantity of sugar.

Example 29: A process for making soft-chew tablets in accordance with certain aspects of the present invention is provided in Example 29 below. The ingredients corresponding to Example 29 are tabulated in Table 29 with the amount of each ingredient used in the process (i.e., the batch quantity) given in percent-by-weight (% w/w) and in milligrams. In Example 29, the active ingredient is omega-3 oils. Each soft-chew tablet formed by the process of Example 29 has an active strength of omega-3 oils of about 1000 mg. The amount of each ingredient provided in Table 29 corresponds to the formation of a single soft-chew tablet; however, as should be understood by those having ordinary skill in the art, the principles of Example 29 can be used to make more soft-chew tablets by proportionally increasing the amount of the ingredients as necessary to produce the desired quantity of soft-chew tablets.

TABLE 29

| Ingredient Name | Amount Per Unit (mg) | % w/w |
|---|---|---|
| Availom 50 High DHA* | 2000.000 | 50.000% |
| Carnauba wax | 30.000 | 0.750% |
| Citric acid anhydrous | 9.200 | 0.230% |
| Color agent (FD&C red) | 2.350 | 0.059% |
| Croscarmellose sodium | 45.000 | 1.125% |
| Crospovidone | 45.000 | 1.125% |
| Dried glucose syrup | 200.000 | 5.000% |
| Flavor agent (tangerine) | 10.800 | 0.270% |
| Glycerin | 410.000 | 10.250% |
| Maltitol solution | 440.000 | 11.000% |
| Mannitol | 197.650 | 4.941% |
| Milk powder | 200.000 | 5.000% |
| Partially pregelatinized starch | 50.000 | 1.250% |
| Simethicone | 200.000 | 5.000% |
| Sorbitol (powder) | 90.000 | 2.250% |
| Sugar (fine) | 70.000 | 1.750% |
| TOTAL | 4000.000 | 100.000% |

*2000 mg of Availom 50 High DHA contains 1000 mg of Omega 3.

Procedure—Example 29

Step 1: The batch quantities of Availom 50 high DHA, croscarmellose sodium, dried glucose syrup, and sorbitol (powder) along with, about 49% of the batch quantity of mannitol, 50% of the batch quantity of milk powder, and 50% of the batch quantity of flavor agent were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and milk powder along with the batch quantities of crospovidone and partially pregelatinized starch were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of citric acid anhydrous was added to the mixture of Step 7 under continuous stirring.

Step 9: The remaining batch quantity of flavor agent was added to the mixture of Step 8 under continuous stirring.

Step 10: The mixture of Step 9 was stirred until a uniform granulation dispersion was formed.

Step 11: The intragranular ingredient mixture of Step 2 was transferred to a rapid mixer granulator (with the impeller set to a slow speed and the chopper off) and mixed for approximately 10 minutes.

Step 12: The batch quantity of simethicone was slowly added to the mixture of Step 11 in a thin stream under continuous mixing (with the impeller set to a slow speed and the chopper on) with intermittent racking.

Step 13: The uniform granulation dispersion of Step 10 was slowly added to the mixture of Step 12 in a thin stream under continuous mixing (with the impeller set to a slow speed and the chopper on) with intermittent racking to form a wet mass.

Step 14: The wet mass of Step 13 and approximately 75% of the extragranular ingredient mixture of Step 4 were passed through a cone mill to form milled granules. The cone mill was fitted with a 4 mm screen, the knife was in the forward position, and the speed setting was slow.

Step 15: The milled granules of Step 14 along with the remaining extragranular ingredient mixture of Step 4 were co-sifted with a No. 8 ASTM to form granules. The granules were collected in a double-lined polybag.

Step 16: The granules of Step 15 were sifted a second time with a No. 8 ASTM and collected in a double-lined polybag.

Step 17: The granules of Step 16 were lubricated using the carnauba wax of Step 5 for approximately 2-minutes.

Step 18: The granules from Step 17 were compressed using a rotary tablet press equipped with a round-shaped (diameter of approx. 20 mm) PTFE punch to form a compressed tablet.

Step 19: The tablets from Step 18 were coated using the batch quantity of sugar.

Example 30: A process for making soft-chew tablets in accordance with certain aspects of the present invention is provided in Example 30 below. The ingredients corresponding to Example 30 are tabulated in Table 30 with the amount of each ingredient used in the process (i.e., the batch quantity) given in percent-by-weight (% w/w) and in milligrams. In Example 30, the active ingredient is omega-3 oils. Each soft-chew tablet formed by the process of Example 30 has an active strength of omega-3 oils of about 510 mg. The amount of each ingredient provided in Table 30 corresponds to the formation of a single soft-chew tablet; however, as should be understood by those having ordinary skill in the art, the principles of Example 30 can be used to make more soft-chew tablets by proportionally increasing the amount of the ingredients as necessary to produce the desired quantity of soft-chew tablets.

TABLE 30

| Ingredient Name | Amount Per Unit (mg) | % w/w |
|---|---|---|
| Carnauba wax | 14.000 | 0.467% |
| Citric acid anhydrous | 9.200 | 0.307% |
| Color agent (FD&C red) | 2.350 | 0.078% |
| Croscarmellose sodium | 45.000 | 1.500% |
| Crospovidone | 45.000 | 1.500% |
| Dried glucose syrup | 300.000 | 10.000% |
| Flavor agent (mixed berry) | 21.200 | 0.707% |
| Flavor agent (tangerine) | 10.800 | 0.360% |
| Glycerin | 250.000 | 8.333% |
| Maltitol solution | 250.000 | 8.333% |
| Mannitol | 199.450 | 6.648% |
| Milk powder | 250.000 | 8.333% |
| Omega 3 Powder* | 1200.000 | 40.000% |
| Partially pregelatinized starch | 110.000 | 3.667% |
| Simethicone | 150.000 | 5.000% |
| Sorbitol (powder) | 95.000 | 3.167% |
| Sugar (fine) | 48.000 | 1.600% |
| TOTAL | 3000.000 | 100.000% |

*1200 mg of Omega 3 powder contains 510 mg of Omega 3.

Procedure—Example 30

Step 1: The batch quantities of croscarmellose sodium, dried glucose syrup, mannitol, milk powder, and sorbitol (powder) along with, about 73% of the batch quantity of partially pregelatinized starch, 55% of the batch quantity of flavor agent (mixed berry), 50% of the batch quantity of flavor agent (tangerine), and 50% of the batch quantity of omega 3 powder were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of flavor agent (tangerine), omega 3 powder, and partially pregelatinized starch, along with the batch quantity of crospovidone were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of citric acid anhydrous was added to the mixture of Step 7 under continuous stirring.

Step 9: The remaining batch quantity of flavor agent (mixed berry) was added to the mixture of Step 8 under continuous stirring.

Step 10: The mixture of Step 9 was stirred until a uniform granulation dispersion was formed.

Step 11: The intragranular ingredient mixture of Step 2 was transferred to a rapid mixer granulator (with the impeller set to a slow speed and the chopper off) and mixed for approximately 10 minutes.

Step 12: The batch quantity of simethicone was slowly added to the mixture of Step 11 in a thin stream under continuous mixing (with the impeller set to a slow speed and the chopper on) with intermittent racking.

Step 13: The uniform granulation dispersion of Step 10 was slowly added to the mixture of Step 12 in a thin stream under continuous mixing (with the impeller set to a slow speed and the chopper on) with intermittent racking to form a wet mass.

Step 14: The wet mass of Step 13 and approximately 75% of the extragranular ingredient mixture of Step 4 were passed through a cone mill to form milled granules. The cone mill was fitted with a 4 mm screen, the knife was in the forward position, and the speed setting was slow.

Step 15: The milled granules of Step 14 along with the remaining extragranular ingredient mixture of Step 4 were co-sifted with a No. 8 ASTM to form granules. The granules were collected in a double-lined polybag.

Step 16: The granules of Step 15 were sifted a second time with a No. 8 ASTM and collected in a double-lined polybag.

Step 17: The granules of Step 16 were lubricated using the carnauba wax of Step 5 for approximately 2-minutes.

Step 18: The granules from Step 17 were compressed using a rotary tablet press equipped with a round-shaped (diameter of approx. 20 mm) PTFE punch to form a compressed tablet.

Step 19: The tablets from Step 18 were coated using the batch quantity of sugar.

Example 31: A process for making soft-chew tablets in accordance with certain aspects of the present invention is provided in Example 31 below. The ingredients corresponding to Example 31 are tabulated in Table 31 with the amount of each ingredient used in the process (i.e., the batch quantity) given in percent-by-weight (% w/w) and in milligrams. In Example 31, the active ingredient is acetaminophen. Each soft-chew tablet formed by the process of Example 31 has an active strength of acetaminophen of about 527 mg. The amount of each ingredient provided in Table 31 corresponds to the formation of a single soft-chew tablet; however, as should be understood by those having ordinary skill in the art, the principles of Example 31 can be used to necessary to produce the desired quantity of soft-chew tablets.

TABLE 31

| Ingredient Name | Amount Per Unit (mg) | % w/w |
| --- | --- | --- |
| Acetaminophen | 526.840 | 15.053% |
| Calcium gluconate monohydrate | 62.500 | 1.786% |
| Carnauba wax | 37.500 | 1.071% |
| Citric acid anhydrous | 26.000 | 0.743% |
| Color agent (FD&C red) | 0.800 | 0.023% |
| Croscarmellose sodium | 120.000 | 3.429% |
| Crospovidone | 100.000 | 2.857% |
| Dried glucose syrup | 625.000 | 17.857% |
| Fine sugar | 63.000 | 1.800% |
| Flavor agent (mixed berry) | 39.000 | 1.114% |
| Glycerin | 219.500 | 6.271% |
| Magnesium stearate | 30.000 | 0.857% |
| Maltitol solution | 204.000 | 5.829% |
| Maltodextrin | 60.000 | 1.714% |
| Mannitol | 454.450 | 12.984% |
| Partially pregelatinized starch | 228.000 | 6.514% |
| Polyethylene glycol | 75.000 | 2.143% |
| Sodium bicarbonate | 20.000 | 0.571% |
| Sorbitol powder | 250.000 | 7.143% |
| Sucralose | 9.250 | 0.264% |
| Xylitol | 349.160 | 9.976% |
| TOTAL | 3500.000 | 100.000% |

Procedure—Example 31

Step 1: The batch quantities of acetaminophen, calcium gluconate monohydrate, carnauba wax, croscarmellose sodium, dried glucose syrup, maltodextrin, sodium bicarbonate, sorbitol powder, and xylitol along with, about 86.0% of the batch quantity of sucralose, 81.0% of the batch quantity of citric acid anhydrous, 72.0% of the batch quantity of partially pregelatinized starch, 68.0% of the batch quantity of mannitol, 26.0% of the batch quantity of flavor agent, and 17.0% of the batch quantity of magnesium stearate were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and partially pregelatinized starch, along with the batch quantity of crospovidone and about 41% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The remaining batch quantity of magnesium stearate was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The remaining batch quantities of sucralose, citric acid anhydrous, and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of polyethylene glycol was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the magnesium stearate of Step 5 for approximately 2-minutes.

Step 17: The granules from Step 16 were compressed using a rotary tablet press equipped with a round-shaped (diameter of approx. 22 mm) PTFE punch, having "C1" embossed on one side, to form a compressed tablet.

Step 18: The tablets from Step 17 were coated using the batch quantity of sugar.

Example 32: A process for making soft-chew tablets in accordance with certain aspects of the present invention is provided in Example 32 below. The ingredients corresponding to Example 32 are tabulated in Table 32 with the amount of each ingredient used in the process (i.e., the batch quantity) given in percent-by-weight (% w/w) and in milligrams. In Example 32, the active ingredient is acetaminophen. Each soft-chew tablet formed by the process of Example 32 has an active strength of acetaminophen of about 521 mg. The amount of each ingredient provided in Table 32 corresponds to the formation of a single soft-chew tablet; however, as should be understood by those having ordinary skill in the art, the principles of Example 32 can be used to make more soft-chew tablets by proportionally increasing the amount of the ingredients as necessary to produce the desired quantity of soft-chew tablets.

TABLE 32

| Ingredient Name | Amount Per Unit (mg) | % w/w |
| --- | --- | --- |
| Acetaminophen | 521.350 | 13.034% |
| Calcium gluconate monohydrate | 50.000 | 1.250% |
| Carnauba wax | 145.000 | 3.625% |
| Citric acid anhydrous | 30.000 | 0.750% |
| Color agent (FD&C red) | 4.750 | 0.119% |
| Croscarmellose sodium | 85.000 | 2.125% |
| Crospovidone | 85.000 | 2.125% |
| Dried glucose syrup | 600.000 | 15.000% |
| Flavor agent (mixed berry) | 55.000 | 1.375% |
| Flavor agent (Rosemary) | 3.000 | 0.075% |
| Glycerin | 450.000 | 11.250% |
| Maltitol solution | 424.530 | 10.613% |
| Mannitol | 418.370 | 10.459% |

TABLE 32-continued

| Ingredient Name | Amount Per Unit (mg) | % w/w |
| --- | --- | --- |
| Milk powder | 470.000 | 11.750% |
| Partially pregelatinized starch | 250.000 | 6.250% |
| Simethicone | 100.000 | 2.500% |
| Sorbitol powder | 200.000 | 5.000% |
| Sucralose | 8.000 | 0.200% |
| Sugar (caster sugar) | 100.000 | 2.500% |
| TOTAL | 4000.000 | 100.000% |

Procedure—Example 32

Step 1: The batch quantities of acetaminophen, calcium gluconate monohydrate, croscarmellose sodium, dried glucose syrup, and sorbitol powder along with, about 83% of the batch quantity of carnauba wax, 80% of the batch quantity of partially pregelatinized starch, 69% of the batch quantity of mannitol, and 68% of the batch quantity of milk powder were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone and about 54% of the batch quantity of flavor agent (mixed berry) were co-sifted with a No. 30 ASTM.

Step 4: The sifted ingredients of Step 3 were sifted a second time with a No. 30 ASTM to form an extragranular ingredient mixture, which was collected in a polybag.

Step 5: The remaining batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantities of citric acid anhydrous, flavor agent (rosemary), and sucralose along with the remaining batch quantity of flavor agent (mixed berry) were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 22 mm) PTFE punch, having "C1" embossed on one side, to form a compressed tablet.

Step 18: The tablets from Step 17 were coated using the batch quantity of sugar.

Example 33: A process for making soft-chew tablets in accordance with certain aspects of the present invention is provided in Example 33 below. The ingredients corresponding to Example 33 are tabulated in Table 33 with the amount of each ingredient used in the process (i.e., the batch quantity) given in percent-by-weight (% w/w) and in milligrams. In Example 33, the active ingredients are dextromethorphan HBr and acetaminophen. Each soft-chew tablet formed by the process of Example 33 has an active strength of dextromethorphan HBr of approximately 15 mg and an active strength of acetaminophen of about 339 mg. The amount of each ingredient provided in Table 33 corresponds to the formation of a single soft-chew tablet; however, as should be understood by those having ordinary skill in the art, the principles of Example 33 can be used to necessary to produce the desired quantity of soft-chew tablets.

TABLE 33

| Ingredient Name | Amount Per Unit (mg) | % w/w |
|---|---|---|
| Acetaminophen | 338.880 | 8.918% |
| Bitter masker | 20.000 | 0.526% |
| Calcium gluconate monohydrate | 60.000 | 1.579% |
| Carnauba wax | 145.000 | 3.816% |
| Color agent (FD&C blue) | 0.008 | 0.000% |
| Crospovidone | 85.000 | 2.237% |
| Dextromethorphan HBr complex | 45.000 | 1.184% |
| Dried glucose syrup | 600.000 | 15.789% |
| Flavor agent (cool eucalyptus) | 18.000 | 0.474% |
| Flavor agent (cool mint) | 9.000 | 0.237% |
| Glycerin | 430.000 | 11.316% |
| Maltitol solution | 430.000 | 11.316% |
| Mannitol | 602.112 | 15.845% |
| Partially pregelatinized starch | 300.000 | 7.895% |
| Simethicone | 100.000 | 2.632% |
| Sodium starch glycolate | 85.000 | 2.237% |
| Sorbitol powder | 420.000 | 11.053% |
| Sucralose | 12.000 | 0.316% |
| Sugar (caster sugar) | 100.000 | 2.632% |
| TOTAL | 3800.000 | 100.000% |

Procedure—Example 33

Step 1: The batch quantities of acetaminophen, calcium gluconate monohydrate, dextromethorphan HBr complex, dried glucose syrup, sodium starch glycolate, and sorbitol powder along with, about 83% of the batch quantity of carnauba wax, 67% of the batch quantity of partially pregelatinized starch, and 62% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and partially pregelatinized starch, along with the batch quantities of crospovidone and flavor agent (cool mint) were co-sifted with a No. 30 ASTM.

Step 4: The sifted ingredients of Step 3 were sifted a second time with a No. 30 ASTM to form an extragranular ingredient mixture, which was collected in a polybag.

Step 5: The remaining batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantities of bitter masker, sucralose, and flavor agent (cool *eucalyptus*) were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 4 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 22 mm) PTFE punch, having "C1" embossed on one side, to form a compressed tablet.

Step 18: The tablets from Step 17 were coated using the batch quantity of sugar.

Example 34: A process for making soft-chew tablets in accordance with certain aspects of the present invention is provided in Example 34 below. The ingredients corresponding to Example 34 are tabulated in Table 34 with the amount of each ingredient used in the process (i.e., the batch quantity) given in percent-by-weight (% w/w) and in milligrams. In Example 34, the active ingredients are dextromethorphan HBr and acetaminophen. Each soft-chew tablet formed by the process of Example 34 has an active strength of dextromethorphan HBr of approximately 15 mg and an active strength of acetaminophen of about 339 mg. The amount of each ingredient provided in Table 34 corresponds to the formation of a single soft-chew tablet; however, as should be understood by those having ordinary skill in the art, the principles of Example 34 can be used to necessary to produce the desired quantity of soft-chew tablets.

TABLE 34

| Ingredient Name | Amount Per Unit (mg) | % w/w |
|---|---|---|
| Acetaminophen | 338.880 | 8.918% |
| Bitter masker | 20.000 | 0.526% |
| Calcium gluconate monohydrate | 60.000 | 1.579% |
| Carnauba wax | 145.000 | 3.816% |
| Citric acid anhydrous | 15.000 | 0.395% |
| Color agent (FD&C red) | 5.000 | 0.132% |
| Crospovidone | 85.000 | 2.237% |
| Dextromethorphan HBr complex | 45.000 | 1.184% |
| Dried glucose syrup | 600.000 | 15.789% |
| Flavor agent (mixed berry) | 55.000 | 1.447% |
| Glycerin | 430.000 | 11.316% |
| Maltitol solution | 420.000 | 11.053% |
| Mannitol | 398.120 | 10.477% |
| Milk powder | 450.000 | 11.842% |
| Partially pregelatinized starch | 250.000 | 6.579% |
| Simethicone | 100.000 | 2.632% |
| Sodium starch glycolate | 85.000 | 2.237% |
| Sorbitol powder | 190.000 | 5.000% |
| Sucralose | 8.000 | 0.211% |
| Sugar (caster sugar) | 100.000 | 2.632% |
| TOTAL | 3800.000 | 100.000% |

Procedure—Example 34

Step 1: The batch quantities of acetaminophen, calcium gluconate monohydrate, dextromethorphan HBr complex, dried glucose syrup, sodium starch glycolate, and sorbitol powder along with, about 83% of the batch quantity of carnauba wax, 80% of the batch quantity of partially pregelatinized starch, 67% of the batch quantity of mannitol, and 67% of the batch quantity of milk powder were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone and about 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The remaining batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantities of bitter masker, citric acid anhydrous, and sucralose along with the remaining batch quantity of flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 22 mm) PTFE punch, having "C1" embossed on one side, to form a compressed tablet.

Step 18: The tablets from Step 17 were coated using the batch quantity of sugar.

Example 35: A process for making soft-chew tablets in accordance with certain aspects of the present invention is provided in Example 35 below. The ingredients corresponding to Example 35 are tabulated in Table 35 with the amount of each ingredient used in the process (i.e., the batch quantity) given in percent-by-weight (% w/w) and in milligrams. In Example 35, the active ingredients are dextromethorphan HBr and acetaminophen. Each soft-chew tablet formed by the process of Example 35 has an active strength of dextromethorphan HBr of approximately 15 mg and an active strength of acetaminophen of about 342 mg. The amount of each ingredient provided in Table 35 corresponds to the formation of a single soft-chew tablet; however, as should be understood by those having ordinary skill in the art, the principles of Example 35 can be used to necessary to produce the desired quantity of soft-chew tablets.

TABLE 35

| Ingredient Name | Amount Per Unit (mg) | % w/w |
|---|---|---|
| Acetaminophen | 342.446 | 9.784% |
| Bitter masker | 25.000 | 0.714% |
| Calcium gluconate monohydrate | 62.500 | 1.786% |
| Carnauba wax | 75.000 | 2.143% |
| Citric acid anhydrous | 13.650 | 0.390% |
| Color agent (FD&C red) | 0.800 | 0.023% |
| Croscarmellose sodium | 120.000 | 3.429% |
| Crospovidone | 100.000 | 2.857% |
| Dextromethorphan HBr complex | 45.000 | 1.286% |
| Dried glucose syrup | 625.000 | 17.857% |
| Flavor agent (mixed berry) | 35.500 | 1.014% |
| Glycerin | 212.500 | 6.071% |
| Magnesium stearate | 3.250 | 0.093% |
| Maltitol solution | 201.000 | 5.743% |
| Maltodextrin | 39.000 | 1.114% |
| Mannitol | 465.000 | 13.286% |
| Partially pregelatinized starch | 203.000 | 5.800% |
| Polyethylene glycol | 75.000 | 2.143% |
| Sodium bicarbonate | 13.000 | 0.371% |
| Sorbitol powder | 436.400 | 12.469% |
| Sucralose | 7.000 | 0.200% |
| Sugar (caster sugar) | 63.000 | 1.800% |
| Xylitol | 336.954 | 9.627% |
| TOTAL | 3500.000 | 100.000% |

Procedure—Example 35

Step 1: The batch quantities of acetaminophen, calcium gluconate monohydrate, citric acid anhydrous, croscarmellose sodium, dextromethorphan HBr complex, dried glucose syrup, magnesium stearate, maltodextrin, sodium bicarbonate, and sorbitol powder along with, about 74% of the batch quantity of sucralose, 73% of the batch quantity of mannitol, 69% of the batch quantity of partially pregelatinized starch, 67% of the batch quantity of carnauba wax, 67% of the batch quantity of xylitol, and 18% of the batch quantity of flavor agent were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, partially pregelatinized starch, and xylitol along with the batch quantity of crospovidone and about 45% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The remaining batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of bitter masker along with the remaining batch quantities of sucralose and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of polyethylene glycol was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 22 mm) PTFE punch, having "C1" embossed on one side, to form a compressed tablet.

Step 18: The tablets from Step 17 were coated using the batch quantity of sugar.

Example 36: A process for making soft-chew tablets in accordance with certain aspects of the present invention is provided in Example 36 below. The ingredients corresponding to Example 36 are tabulated in Table 36 with the amount of each ingredient used in the process (i.e., the batch quantity) given in percent-by-weight (% w/w) and in milligrams. In Example 36, the active ingredient is dextromethorphan HBr. Each soft-chew tablet formed by the process of Example 36 has an active strength of dextromethorphan HBr of about 15 mg. The amount of each ingredient provided in Table 36 corresponds to the formation of a single soft-chew tablet; however, as should be understood by those having ordinary skill in the art, the principles of Example 36 can be used to make more soft-chew tablets by proportionally increasing the amount of the ingredients as necessary to produce the desired quantity of soft-chew tablets.

TABLE 36

| Ingredient Name | Amount Per Unit (mg) | % w/w |
|---|---|---|
| Bitter masker | 10.000 | 0.513% |
| Calcium gluconate monohydrate | 25.000 | 1.282% |
| Carnauba wax | 90.000 | 4.615% |
| Color agent (FD&C red) | 2.650 | 0.136% |
| Croscarmellose sodium | 53.000 | 2.718% |
| Crospovidone | 53.000 | 2.718% |
| Dextromethorphan HBr complex | 45.000 | 2.308% |
| Dried glucose syrup | 300.000 | 15.385% |
| Flavor agent (mixed berry) | 23.200 | 1.190% |
| Glycerin | 219.000 | 11.231% |
| Maltitol solution | 229.000 | 11.744% |
| Mannitol | 233.880 | 11.994% |
| Milk powder | 263.000 | 13.487% |
| Partially pregelatinized starch | 152.000 | 7.795% |
| Simethicone | 100.000 | 5.128% |
| Sorbitol powder | 100.000 | 5.128% |
| Sucralose | 1.270 | 0.065% |
| Sugar (caster sugar) | 50.000 | 2.564% |
| TOTAL | 1950.000 | 100.000% |

Procedure—Example 36

Step 1: The batch quantities of calcium gluconate monohydrate, croscarmellose sodium, dextromethorphan HBr complex, dried glucose syrup, and sorbitol powder along with, about 79% of the batch quantity of partially pregelatinized starch, 76% of the batch quantity of milk powder, and 73% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, milk powder, and partially pregelatinized starch, along with the batch quantity of crospovidone and about 54% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantities of bitter masker and sucralose along with the remaining batch quantity of flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 20 mm) PTFE punch to form a compressed tablet.

Step 18: The tablets from Step 17 were coated using the batch quantity of sugar.

Example 37: A process for making soft-chew tablets in accordance with certain aspects of the present invention is provided in Example 37 below. The ingredients corresponding to Example 37 are tabulated in Table 37 with the amount of each ingredient used in the process (i.e., the batch quantity) given in percent-by-weight (% w/w) and in milligrams. In Example 37, the active ingredient is dextromethorphan HBr. Each soft-chew tablet formed by the process of Example 37 has an active strength of dextromethorphan HBr of about 15 mg. The amount of each ingredient provided in Table 37 corresponds to the formation of a single soft-chew tablet; however, as should be understood by those having ordinary skill in the art, the principles of Example 37 can be used to make more soft-chew tablets by proportionally increasing the amount of the ingredients as necessary to produce the desired quantity of soft-chew tablets.

TABLE 37

| Ingredient Name | Amount Per Unit (mg) | % w/w |
|---|---|---|
| Bitter masker | 6.000 | 0.300% |
| Calcium gluconate monohydrate | 50.000 | 2.500% |
| Citric acid anhydrous | 4.000 | 0.200% |
| Color agent (FD&C blue) | 0.100 | 0.005% |
| Color agent (FD&C red) | 0.900 | 0.045% |
| Corn oil | 60.000 | 3.000% |
| Crospovidone | 60.000 | 3.000% |
| Dextromethorphan HBr complex | 45.000 | 2.250% |
| Dried glucose syrup | 400.000 | 20.000% |
| Glycerin | 220.000 | 11.000% |
| Flavor agent (grape) | 23.000 | 1.150% |
| Magnesium stearate | 20.000 | 1.000% |
| Maltitol solution | 200.000 | 10.000% |

TABLE 37-continued

| Ingredient Name | Amount Per Unit (mg) | % w/w |
|---|---|---|
| Mannitol | 429.800 | 21.490% |
| Partially pregelatinized starch | 170.000 | 8.500% |
| Sodium starch glycolate | 60.000 | 3.000% |
| Sorbitol powder | 200.000 | 10.000% |
| Sucralose | 1.200 | 0.060% |
| Sugar (caster sugar) | 50.000 | 2.500% |
| TOTAL | 2000.000 | 100.000% |

Procedure—Example 37

Step 1: The batch quantities of calcium gluconate monohydrate, dextromethorphan HBr complex, dried glucose syrup, sodium starch glycolate, and sorbitol powder along with, about 71% of the batch quantity of partially pregelatinized starch and 53% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and partially pregelatinized starch, along with the batch quantity of crospovidone and about 57% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of magnesium stearate was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantities of bitter masker, citric acid anhydrous, and sucralose along with the remaining batch quantity of flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of corn oil was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the magnesium stearate of Step 5 for approximately 2-minutes.

Step 17: The granules from Step 16 were compressed using a rotary tablet press equipped with a round-shaped (diameter of approx. 20 mm) PTFE punch to form a compressed tablet.

Step 18: The tablets from Step 17 were coated using the batch quantity of sugar.

Example 38: A process for making soft-chew tablets in accordance with certain aspects of the present invention is provided in Example 38 below. The ingredients corresponding to Example 38 are tabulated in Table 38 with the amount of each ingredient used in the process (i.e., the batch quantity) given in percent-by-weight (% w/w) and in milligrams. In Example 38, the active ingredient is levocetirizine dihydrochloride. Each soft-chew tablet formed by the process of Example 38 has an active strength of levocetirizine dihydrochloride of about 10 mg. The amount of each ingredient provided in Table 38 corresponds to the formation of a single soft-chew tablet; however, as should be understood by those having ordinary skill in the art, the principles of Example 38 can be used to make more soft-chew tablets by proportionally increasing the amount of the ingredients as necessary to produce the desired quantity of soft-chew tablets.

TABLE 38

| Ingredient Name | Amount Per Unit (mg) | % w/w |
|---|---|---|
| Calcium gluconate monohydrate | 25.000 | 2.500% |
| Carnauba wax | 15.000 | 1.500% |
| Citric acid anhydrous | 2.000 | 0.200% |
| Color agent (FD&C blue) | 0.100 | 0.010% |
| Color agent (FD&C red) | 0.400 | 0.040% |
| Dried glucose syrup | 220.000 | 22.000% |
| Flavor agent (grape) | 9.000 | 0.900% |
| Glycerin | 90.000 | 9.000% |
| Levocetirizine dihydrochloride complex | 40.000 | 4.000% |
| Magnesium stearate | 10.000 | 1.000% |
| Maltitol solution | 80.000 | 8.000% |
| Mannitol | 253.000 | 25.300% |
| MCT oil | 30.000 | 3.000% |
| Partially pregelatinized starch | 100.000 | 10.000% |
| Sorbitol powder | 100.000 | 10.000% |
| Sucralose | 0.500 | 0.050% |
| Sugar (caster sugar) | 25.000 | 2.500% |
| TOTAL | 1000.000 | 100.000% |

Procedure—Example 38

Step 1: The batch quantities of calcium gluconate monohydrate, carnauba wax, dried glucose syrup, levocetirizine dihydrochloride complex, and sorbitol powder along with, about 75% of the batch quantity of partially pregelatinized starch and 60% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and partially pregelatinized starch, along with about 67% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The batch quantity of magnesium stearate was sifted using a No. 60 ASTM and collected in a polybag.

Step 6: The batch quantity of maltitol solution was added to the batch quantity of glycerin under continuous stirring.

Step 7: The batch quantity of color agents was added to the mixture of Step 6 under continuous stirring.

Step 8: The batch quantities of citric acid anhydrous and sucralose along with the remaining batch quantity of flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of MCT oil was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the magnesium stearate of Step 5 for approximately 2-minutes.

Step 17: The granules from Step 16 were compressed using a rotary tablet press equipped with a round-shaped (diameter of approx. 22 mm) PTFE punch to form a compressed tablet.

Step 18: The tablets from Step 17 were coated using the batch quantity of sugar.

Example 39: A process for making soft-chew tablets in accordance with certain aspects of the present invention is provided in Example 39 below. The ingredients corresponding to Example 39 are tabulated in Table 39 with the amount of each ingredient used in the process (i.e., the batch quantity) given in percent-by-weight (% w/w) and in milligrams. In Example 39, the active ingredients are diphenhydramine HCl and acetaminophen. Each soft-chew tablet formed by the process of Example 39 has an active strength of diphenhydramine HCl of approximately 83 mg and an active strength of acetaminophen of about 339 mg. The amount of each ingredient provided in Table 39 corresponds to the formation of a single soft-chew tablet; however, as should be understood by those having ordinary skill in the art, the principles of Example 39 can be used to necessary to produce the desired quantity of soft-chew tablets.

TABLE 39

| Ingredient Name | Amount Per Unit (mg) | % w/w |
|---|---|---|
| Acetaminophen | 338.880 | 8.918% |
| Bitter masker | 20.000 | 0.526% |

TABLE 39-continued

| Ingredient Name | Amount Per Unit (mg) | % w/w |
| --- | --- | --- |
| Calcium gluconate monohydrate | 60.000 | 1.579% |
| Carnauba wax | 145.000 | 3.816% |
| Citric acid anhydrous | 15.000 | 0.395% |
| Color agent (FD&C red) | 5.000 | 0.132% |
| Crospovidone | 85.000 | 2.237% |
| Diphenhydramine HCl beads | 82.550 | 2.172% |
| Dried glucose syrup | 600.000 | 15.789% |
| Flavor agent (mixed berry) | 55.000 | 1.447% |
| Glycerin | 450.000 | 11.842% |
| Maltitol solution | 420.000 | 11.053% |
| Mannitol | 558.570 | 14.699% |
| Partially pregelatinized starch | 250.000 | 6.579% |
| Simethicone | 100.000 | 2.632% |
| Sodium starch glycolate | 85.000 | 2.237% |
| Sorbitol powder | 420.000 | 11.053% |
| Sucralose | 10.000 | 0.263% |
| Sugar (caster sugar) | 100.000 | 2.632% |
| TOTAL | 3800.000 | 100.000% |

Procedure—Example 39

Step 1: The batch quantities of acetaminophen, calcium gluconate monohydrate, diphenhydramine HCl beads, dried glucose syrup, sodium starch glycolate, and sorbitol powder along with, about 83% of the batch quantity of carnauba wax, 80% of the batch quantity of partially pregelatinized starch, and 50% of the batch quantity of mannitol were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol and partially pregelatinized starch, along with the batch quantity of crospovidone and about 55% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The remaining batch quantity of carnauba wax was sifted using a No. 60 ASTM and collected in a polybag.

Step 6: The batch quantity of maltitol solution was added to the batch quantity of glycerin under continuous stirring.

Step 7: The batch quantities of the color agents were added to the mixture of Step 6 under continuous stirring.

Step 8: The batch quantities of bitter masker, citric acid anhydrous, and sucralose along with the remaining batch quantity of flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of simethicone was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 22 mm) PTFE punch, having "C1" embossed on one side, to form a compressed tablet.

Step 18: The tablets from Step 17 were coated using the batch quantity of sugar.

Example 40: A process for making soft-chew tablets in accordance with certain aspects of the present invention is provided in Example 40 below. The ingredients corresponding to Example 40 are tabulated in Table 40 with the amount of each ingredient used in the process (i.e., the batch quantity) given in percent-by-weight (% w/w) and in milligrams. In Example 40, the active ingredients are diphenhydramine HCl and acetaminophen. Each soft-chew tablet formed by the process of Example 40 has an active strength of diphenhydramine HCl of approximately 86 mg and an active strength of acetaminophen of about 342 mg. The amount of each ingredient provided in Table 40 corresponds to the formation of a single soft-chew tablet; however, as should be understood by those having ordinary skill in the art, the principles of Example 40 can be used to necessary to produce the desired quantity of soft-chew tablets.

TABLE 40

| Ingredient Name | Amount Per Unit (mg) | % w/w |
| --- | --- | --- |
| Acetaminophen complex | 342.446 | 9.784% |
| Bitter masker | 25.000 | 0.714% |
| Calcium gluconate monohydrate | 70.000 | 2.000% |
| Carnauba wax | 75.000 | 2.143% |
| Citric acid anhydrous | 13.650 | 0.390% |
| Color agent (FD&C red) | 0.800 | 0.023% |
| Croscarmellose sodium | 120.000 | 3.429% |
| Crospovidone | 100.000 | 2.857% |
| Diphenhydramine HCl beads | 85.550 | 2.444% |
| Dried glucose syrup | 625.000 | 17.857% |
| Flavor agent (mixed berry) | 37.500 | 1.071% |
| Glycerin | 215.000 | 6.143% |
| Magnesium stearate | 3.250 | 0.093% |
| Maltitol solution | 200.000 | 5.714% |
| Maltodextrin | 39.000 | 1.114% |
| Mannitol | 440.000 | 12.571% |
| Partially pregelatinized starch | 203.000 | 5.800% |
| Polyethylene glycol | 75.000 | 2.143% |
| Sodium bicarbonate | 13.000 | 0.371% |
| Sorbitol powder | 409.850 | 11.710% |
| Sucralose | 7.000 | 0.200% |
| Sugar (caster sugar) | 63.000 | 1.800% |
| Xylitol | 336.950 | 9.627% |
| TOTAL | 3500.000 | 100.000% |

Procedure—Example 40

Step 1: The batch quantities of acetaminophen, calcium gluconate monohydrate, citric acid anhydrous, croscarmellose sodium, diphenhydramine beads, dried glucose syrup, magnesium stearate, maltodextrin, sodium bicarbonate, and sorbitol powder along with, about 73% of the batch quantity of mannitol, 69% of the batch quantity of partially pregelatinized starch, 67% of the batch quantity of carnauba wax, 67% of the batch quantity of xylitol, 65% of the batch quantity of sucralose, and 17% of the batch quantity of flavor agent were co-sifted with a No. 30 ASTM.

Step 2: The sifted ingredients of Step 1 were sifted a second time with a No. 30 ASTM to form an intragranular ingredient mixture, which was collected in a polybag.

Step 3: The remaining batch quantities of mannitol, partially pregelatinized starch, and xylitol along with the batch quantity of crospovidone and about 43% of the batch quantity of flavor agent were co-sifted with a No. 30 ASTM.

Step 4: The sifted ingredients of Step 3 were sifted a second time with a No. 30 ASTM to form an extragranular ingredient mixture, which was collected in a polybag.

Step 5: The remaining batch quantity of carnauba wax was sifted using a No. 60 ASTM and collected in a polybag.

Step 6: The batch quantity of maltitol solution was added to the batch quantity of glycerin under continuous stirring.

Step 7: The batch quantity of color agent was added to the mixture of Step 6 under continuous stirring.

Step 8: The batch quantity of bitter masker along with the remaining batch quantities of sucralose and flavor agent were added to the mixture of Step 7 under continuous stirring.

Step 9: The mixture of Step 8 was stirred until a uniform granulation dispersion was formed.

Step 10: The intragranular ingredient mixture of Step 2 was transferred to a rapid mixer granulator (with the impeller set to a slow speed and the chopper off) and mixed for approximately 10 minutes.

Step 11: The batch quantity of polyethylene glycol was slowly added to the mixture of Step 10 in a thin stream under continuous mixing (with the impeller set to a slow speed and the chopper on) with intermittent racking.

Step 12: The uniform granulation dispersion of Step 9 was slowly added to the mixture of Step 11 in a thin stream under continuous mixing (with the impeller set to a slow speed and the chopper on) with intermittent racking to form a wet mass.

Step 13: The wet mass of Step 12 and approximately 75% of the extragranular ingredient mixture of Step 4 were passed through a cone mill to form milled granules. The cone mill was fitted with a 3 mm screen, the knife was in the forward position, and the speed setting was slow.

Step 14: The milled granules of Step 13 along with the remaining extragranular ingredient mixture of Step 4 were co-sifted with a No. 8 ASTM to form granules. The granules were collected in a double-lined polybag.

Step 15: The granules of Step 14 were sifted a second time with a No. 8 ASTM and collected in a double-lined polybag.

Step 16: The granules of Step 15 were lubricated using the carnauba wax of Step 5 for approximately 2-minutes.

Step 17: The granules from Step 16 were compressed using a rotary tablet press equipped with a round-shaped (diameter of approx. 22 mm) PTFE punch, having "C1" embossed on one side, to form a compressed tablet.

Step 18: The tablets from Step 17 were coated using the batch quantity of sugar.

ANALYSIS

The results of a product characterization analysis performed on the soft chewable tablets formed in accordance with the Examples provided herein is summarized in Table D1. Table D1 provides information pertaining to the product characterization analysis of the soft chewable tablets formed in accordance with the corresponding Examples provided therein shortly after compression.

TABLE D1

| Example # | Tablet Mass (mg) | Thickness (mm) | Hardness (N) | Friability (%) |
|---|---|---|---|---|
| 1 | 2034 to 2060 | 7.83 to 7.88 | 0.00 | 0.00 |
| 2 | 1890 to 1925 | 8.25 to 8.39 | 0.00 | 0.00 |
| 2* | 1941 to 1970 | 8.41 to 8.46 | 0.00 | |
| 3 | 1890 to 1925 | 8.25 to 8.39 | 0.00 | 0.00 |
| 3* | 1941 to 1970 | 8.41 to 8.46 | 0.00 | |
| 4 | 1860 to 1935 | 8.25 to 8.29 | 0.00 | 0.00 |
| 4* | 1917 to 1955 | 8.27 to 8.36 | 0.00 | |
| 5 | 1855 to 1930 | 8.21 to 8.26 | 0.00 | 0.00 |
| 5* | 1947 to 1963 | 8.29 to 8.32 | 0.00 | |
| 6 | 1890 to 1925 | 8.25 to 8.39 | 0.00 | 0.00 |
| 6* | 1941 to 1970 | 8.41 to 8.46 | 0.00 | |
| 7 | 1897 to 1926 | 8.26 to 8.31 | 0.00 | 0.00 |
| 7* | 1936 to 1988 | 8.31 to 8.36 | 0.00 | |
| 8 | 1866 to 1936 | 8.23 to 8.33 | 0.00 | 0.00 |
| 8* | 1919 to 1986 | 8.34 to 8.39 | 0.00 | |
| 9 | 2800 | 8.35 to 8.39 | 0.00 | 0.00 |
| 10 | 3691 to 3735 | 9.2 to 9.4 | 0.00 | 0.00 |
| 10* | 3788 to 3835 | 9.5 to 9.7 | 0.00 | |
| 11 | 3775 to 3861 | 8.6 to 8.8 | 0.00 | 0.00 |
| 11* | 3865 to 3936 | 9.0 to 9.1 | 0.00 | |
| 12 | 3781 to 3855 | 8.6 to 8.8 | 0.00 | 0.00 |
| 12* | 3867 to 3945 | 9.1 to 9.3 | 0.00 | |
| 13 | 2510 to 2528 | 7.85 to 7.91 | 0.00 | 0.00 |
| 14 | 2473 to 2579 | 8.43 to 8.45 | 0.00 | 0.00 |
| 14* | 2599 to 2717 | 8.68 to 8.76 | 0.00 | |
| 15 | 2960 to 3074 | 8.51 to 8.60 | 0.00 | 0.00 |
| 15* | 3110 to 3210 | 8.71 to 8.79 | 0.00 | |
| 16 | 861 to 880 | 6.96 to 7.09 | 0.00 | 0.00 |
| 16* | 877 to 925 | 7.26 to 7.35 | 0.00 | |
| 17 | 1695 to 1735 | 8.06 to 8.19 | 0.00 | 0.00 |
| 17* | 1732 to 1781 | 8.26 to 8.36 | 0.00 | |
| 18 | 1050 to 1075 | 7.10 to 7.20 | 0.00 | 0.00 |
| 19 | 960 to 979 | 6.20 to 6.30 | 0.00 | 0.00 |
| 20 | 3165 to 3183 | 8.90 to 8.94 | 0.00 | 0.00 |
| 21 | 4010 to 4040 | 10.58 to 10.96 | 0.00 | 0.00 |
| 22 | 1940 to 1973 | 8.40 to 8.49 | 0.00 | |
| 23 | 3081 to 3126 | 8.90 to 9.00 | 0.00 | |
| 24 | 3122 to 3176 | 9.06 to 9.19 | 0.00 | |
| 25 | 3175 to 3226 | 9.12 to 9.25 | 0.00 | |
| 26 | 2979 to 3041 | 8.86 to 8.92 | 0.00 | |
| 27 | 2964 to 3012 | 8.75 to 8.83 | 0.00 | |
| 28 | 2984 to 3033 | 8.81 to 8.91 | 0.00 | |
| 29 | 3967 to 4057 | 9.4 to 9.8 | 0.00 | |
| 30 | 2963 to 3016 | 8.71 to 8.80 | 0.00 | |
| 31 | 3471 to 3534 | 8.9 to 9.0 | 0.00 | 0.00 |
| 31* | 3520 to 3539 | 9.1 to 9.2 | 0.00 | 0.00 |
| 32 | 3875 to 3918 | 9.3 to 9.4 | 0.00 | 0.00 |
| 32* | 3974 to 4015 | 9.4 to 9.4 | 0.00 | 0.00 |
| 33 | 3691 to 3735 | 9.2 to 9.3 | 0.00 | 0.00 |
| 33* | 3799 to 3845 | 9.3 to 9.4 | 0.00 | 0.00 |
| 34 | 3699 to 3735 | 9.1 to 9.2 | 0.00 | 0.00 |
| 34* | 3785 to 3819 | 9.3 to 9.4 | 0.00 | 0.00 |
| 35 | 3410 to 3464 | 9.0 to 9.1 | 0.00 | 0.00 |
| 35* | 3490 to 3524 | 9.1 to 9.2 | 0.00 | 0.00 |
| 36 | 1877 to 1926 | 8.4 to 8.5 | 0.00 | 0.00 |
| 36* | 1945 to 1987 | 8.6 to 8.7 | 0.00 | 0.00 |
| 37 | 1915 to 1967 | 8.6 to 8.7 | 0.00 | 0.00 |
| 37* | 1977 to 2014 | 8.8 to 8.9 | 0.00 | 0.00 |
| 38 | 960 to 996 | 6.8 to 6.9 | 0.00 | 0.00 |
| 38* | 984 to 1022 | 7.0 to 7.1 | 0.00 | 0.00 |
| 39 | 3677 to 3736 | 9.3 to 9.4 | 0.00 | 0.00 |
| 39* | 3755 to 3845 | 9.4 to 9.5 | 0.00 | 0.00 |
| 40 | 3405 to 3465 | 9.1 to 9.2 | 0.00 | 0.00 |
| 40* | 3505 to 3545 | 9.2 to 9.3 | 0.00 | 0.00 |

*indicates that the tablet tested included a coating.

A texture analysis was performed on the soft chew tablets formed in accordance with the Examples provided herein using a CT3 Texture Analyzer (Brookfield Engineering)

configured as provided in Table D2. Texture parameters derived from the texture analysis are provided in Tables D3 and D4, including values for: average hardness cycle 1 ("AHC1") given in grams; average adhesiveness ("AAd") given in millijoules; average fracturability with 1% load sensitivity ("AF1") given in grams; average hardness cycle 2 ("AHC2") given in grams; average cohesiveness ("ACo") given in millimeters; average springiness ("ASp") given in millimeters; average gumminess ("AGu") given in grams; and average chewiness ("ACh") given in millijoules. Additional details relating to the foregoing parameters and texture analyzer can be found in the Operating Instructions for the CT3 Texture Analyzer (Manual No. M08-372-F1116), which is incorporated herein by reference in its entirety. It should be understood that the present invention is not limited to parameters measured by a specific instrument and that other instruments may be used without departing from the spirit of the present invention.

TABLE D2

| | |
|---|---|
| Target | 6.0 mm |
| Hold time | 0 sec |
| Trigger load | 2 g |
| Test Speed | 2.00 mm/sec |
| Return speed | 2.0 mm/s |
| Number of cycles | 2 |
| Target Type | Distance |
| Recovery | 0 seconds |
| Same Trigger | TRUE |
| Pretest speed | 2.00 mm/sec |
| Data rate | 20.00 points/sec |
| Probe | TA 9 |
| Fixture | TA-STF |
| Load Cell | 25000 g |

TABLE D3

| Ex # | AHC1 | AAd | AF1 | AHC2 |
|---|---|---|---|---|
| 1 | 468 | 0.9 | 468 | 338 |
| 2 | 476 | 2.83 | 472.67 | 364 |
| 3 | 476 | 2.83 | 472.67 | 364 |
| 4 | 341.33 | 0.77 | 331.33 | 222.67 |
| 5 | 192 | 0.2 | 164.67 | 144 |
| 6 | 476 | 2.83 | 472.67 | 364 |
| 7 | 512 | 0.67 | 502 | 339.33 |
| 8 | 248 | 0.3 | 158.67 | 179.33 |
| 9 | 734.6 | 1.5 | 734.7 | 556 |
| 10 | 446 | 1.1 | 322 | 310 |
| 11 | 432 | 3.6 | 432 | 310 |
| 12 | 366 | 1.3 | 366 | 254 |
| 13 | 820 | 1.8 | 820 | 590 |
| 14 | 776 | 6.4 | 776 | 536 |
| 15 | 366 | 1.3 | 366 | 254 |
| 16 | 754 | 1.7 | 754 | 586 |
| 17 | 520 | 1.7 | 516 | 362 |
| 18 | 604 | 1.4 | 604 | 492 |
| 19 | 806 | 1.8 | 806 | 600 |
| 20 | 936 | 1.8 | 936 | 720 |
| 21 | 1728 | 10.7 | 1728 | 1170 |

TABLE D4

| Ex # | ACo | ASp | AGu | ACh |
|---|---|---|---|---|
| 1 | 0.13 | 3.2 | 62 | 2 |
| 2 | 0.14 | 3.56 | 69.67 | 2.5 |
| 3 | 0.14 | 3.56 | 69.67 | 2.5 |
| 4 | 0.12 | 3.73 | 41 | 1.53 |
| 5 | 0.29 | 4.59 | 52.67 | 2.77 |
| 6 | 0.14 | 3.56 | 69.67 | 2.5 |
| 7 | 0.11 | 3.24 | 55.67 | 1.73 |
| 8 | 0.11 | 2.17 | 26.33 | 0.6 |
| 9 | 0.1 | 3.7 | 109 | 3.9 |
| 10 | 0.13 | 3.63 | 56 | 2 |
| 11 | 0.26 | 4.5 | 113 | 5 |
| 12 | 0.17 | 5.73 | 62 | 3.5 |
| 13 | 0.16 | 3.22 | 134 | 4.2 |
| 14 | 0.24 | 4.09 | 188 | 7.6 |
| 15 | 0.17 | 5.73 | 62 | 3.5 |
| 16 | 0.14 | 3.96 | 106 | 4.1 |
| 17 | 0.12 | 3.65 | 61 | 2.2 |
| 18 | 0.17 | 3.56 | 106 | 3.7 |
| 19 | 0.14 | 4.22 | 114 | 4.7 |
| 20 | 0.16 | 3.72 | 151 | 5.5 |
| 21 | 0.19 | 4.63 | 329 | 14.9 |

A disintegration analysis of the soft chew tablets made in accordance with the Examples provided herein was performed in accordance with U.S. Pharmacopeia General Chapter <701> Disintegration. In each instance, the disintegration analysis was performed using nine hundred milliliters (900 ml) of water at a temperature of about 37° C. (±2° C.) and a sample size of six (6) soft chew tablets. Table D5 provides information pertaining to the disintegration analysis of the soft chew tablets formed in accordance with the corresponding Examples provided therein shortly after the compression step. Table D5 includes values for disintegration time ("DT") provided in minutes.

TABLE D5

| Example # | DT |
|---|---|
| 1 | 41 |
| 2 | 36 |
| 2* | 36 |
| 3 | 36 |
| 3* | 36 |
| 4 | 32 |
| 4* | 32 |
| 5 | 30 |
| 5* | 30 |
| 6 | 36 |
| 6 | 35 |
| 6* | 36 |
| 7 | 30 |
| 7* | 35 |
| 8* | 30 |
| 9 | 10 |
| 10 | 28 to 29 |
| 11 | 20 to 21 |
| 12 | 17 to 18 |
| 13 | 2 to 3 |
| 14 | 18 to 19 |
| 15 | 22 to 23 |
| 16 | 13 |
| 17 | 17 to 18 |
| 18 | 15 to 16 |
| 19 | 14 to 15 |
| 20 | 26 to 27 |
| 21 | 28 to 29 |
| 22 | 36 |
| 23 | 30 |
| 24 | 27 |
| 25 | 29 |
| 26 | 27 |
| 27 | 31 |
| 28 | 26 |
| 29 | 36 |
| 30 | 30 |
| 31 | 24 |
| 31* | 26 |
| 32 | 29 |
| 32* | 31 |
| 33 | 26 |

TABLE D5-continued

| Example # | DT |
|---|---|
| 33* | 28 |
| 34 | 22 |
| 34* | 23 |
| 35 | 27 |
| 35* | 27 |
| 36 | 19 |
| 36* | 20 |
| 37 | 21 |
| 37* | 22 |
| 38 | 12 |
| 38* | 13 |
| 39 | 30 |
| 39* | 30 |
| 40 | 27 |
| 40* | 28 |

*indicates that the tablet analyzed included a coating.

The results of a particle size analysis of the tablets are summarized in Table D6.

TABLE D6

| Example | Sieve Size | % retained | Cumulative % retained |
|---|---|---|---|
| 2 | 10 | 14.86 | 14.86 |
| 3 | 10 | 14.86 | 14.86 |
| 4 | 10 | 4.84 | 4.84 |
| 5 | 10 | 5.95 | 5.95 |
| 6 | 10 | 14.86 | 14.86 |
| 7 | 10 | 9.24 | 9.24 |
| 8 | 10 | 5.24 | 5.24 |
| 9 | 10 | 10.8 | 10.8 |
| 22 | 10 | 11.61 | 11.61 |
| 2 | 18 | 42.91 | 57.77 |
| 3 | 18 | 42.91 | 57.77 |
| 4 | 18 | 5.01 | 9.85 |
| 5 | 18 | 6.23 | 12.18 |
| 6 | 18 | 42.91 | 57.77 |
| 7 | 18 | 25.93 | 35.17 |
| 8 | 18 | 21.93 | 27.17 |
| 9 | 18 | 41.18 | 51.97 |
| 22 | 18 | 35.22 | 46.83 |
| 2 | 20 | 18.9 | 76.67 |
| 3 | 20 | 18.9 | 76.67 |
| 4 | 20 | 7.59 | 17.44 |
| 5 | 20 | 8.05 | 20.23 |
| 6 | 20 | 18.9 | 76.67 |
| 7 | 20 | 6.96 | 42.14 |
| 8 | 20 | 14.97 | 42.14 |
| 9 | 20 | 8.82 | 60.8 |
| 22 | 20 | 14.72 | 61.55 |
| 2 | 30 | 20.06 | 96.72 |
| 3 | 30 | 20.06 | 96.72 |
| 4 | 30 | 46.47 | 63.91 |
| 5 | 30 | 49.37 | 69.61 |
| 6 | 30 | 20.06 | 96.72 |
| 7 | 30 | 23.85 | 65.99 |
| 8 | 30 | 39.86 | 81.99 |
| 9 | 30 | 10.84 | 71.64 |
| 22 | 30 | 12.25 | 73.79 |
| 2 | 40 | 3.28 | 100 |
| 3 | 40 | 3.28 | 100 |
| 4 | 40 | 33.67 | 97.58 |
| 5 | 40 | 28.98 | 98.58 |
| 6 | 40 | 3.28 | 100 |
| 7 | 40 | 31.81 | 97.8 |
| 8 | 40 | 19.81 | 101.8 |
| 9 | 40 | 16.36 | 87.99 |
| 22 | 40 | 24.85 | 98.64 |
| 2 | Receiver | 0 | 100 |
| 3 | Receiver | 0 | 100 |
| 4 | Receiver | 2.42 | 100 |
| 5 | Receiver | 1.42 | 100 |
| 6 | Receiver | 0 | 100 |
| 7 | Receiver | 2.2 | 100 |
| 8 | Receiver | 0.36 | 102.16 |
| 9 | Receiver | 12.01 | 100 |
| 22 | Receiver | 1.36 | 100 |

The results of a flow property analysis of the tablets are summarized in Table D7.

TABLE D7

| Ex# | Bulk Density (g/ml) | Tapped Density (g/ml) | Compressibility Index (%) | Bulk Density (g/ml) Hausner's Ratio |
|---|---|---|---|---|
| 2 | 0.56 | 0.69 | 20 | 1.25 |
| 3 | 0.56 | 0.69 | 20 | 1.25 |
| 4 | 0.45 | 0.57 | 20 | 1.25 |
| 5 | 0.47 | 0.58 | 18.87 | 1.23 |
| 6 | 0.56 | 0.69 | 20 | 1.25 |
| 7 | 0.5 | 0.68 | 26 | 1.35 |
| 8 | 0.42 | 0.57 | 26.67 | 1.36 |
| 9 | 0.51 | 0.61 | 16.33 | 1.2 |
| 22 | 0.44 | 0.56 | 21.05 | 1.27 |

ADDITIONAL CONSIDERATIONS

In this disclosure, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

As used in this disclosure, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

As used in this disclosure, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present disclosure uses numerical ranges to quantify certain parameters relating to various embodiments. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds). Furthermore, in the case of all the relative or percentage amount information, particularly weight-related amount information, that this information is to be selected by a person skilled in the art, within the scope of the present invention, in such a manner that the sum of the respective ingredients, active ingredients, additives or ancillary substances or the like always come up to 100% or 100% w/w. However, this is obvious to a person skilled in the art.

This disclosure is to be construed as exemplary only and does not describe every possible embodiment since describing every possible embodiment would be impractical. Numerous alternative embodiments may be implemented, using either current technology or technology developed after the filing date of this patent application, which would still fall within the scope of the present invention.

Although the above description presents features of preferred embodiments of the present invention, other preferred embodiments may also be created in keeping with the principles of the invention. Such other preferred embodiments may, for instance, be provided with features drawn from one or more of the embodiments described above. Yet further, such other preferred embodiments may include features from multiple embodiments described above, particularly where such features are compatible for use together despite having been presented independently as part of separate embodiments in the above description.

The inventors hereby state their intent to rely on the Doctrine of Equivalents to determine and assess the reasonably fair scope of the present invention as pertains to anything not materially departing from but outside the literal scope of the invention as set forth herein.

What is claimed is:

1. A soft-chew tablet comprising at least one active ingredient,
    wherein said tablet is formed using a tablet press,
    wherein said tablet is formed without heating,
    wherein said tablet has a hardness of less than 2 kp when measured on a tablet hardness tester, and
    wherein said tablet has a friability of less than one percent at one-hundred rotations when tested in accordance with USP friability test.

2. The soft-chew tablet as claimed in claim 1, said soft-chew tablet having a weight ranging from 200 mg to 5000 mg.

3. The soft-chew tablet as claimed in claim 1, said active ingredient comprising an active pharmaceutical ingredient.

* * * * *